US011523749B2

(12) United States Patent
Schwartz et al.

(10) Patent No.: US 11,523,749 B2
(45) Date of Patent: *Dec. 13, 2022

(54) SYSTEMS AND METHODS FOR TRACKING AN INTRABODY CATHETER

(71) Applicant: Navix International Limited, Road Town (VG)

(72) Inventors: Yitzhack Schwartz, Haifa (IL); Shlomo Ben-Haim, Marlow (GB); Eli Dichterman, Haifa (IL)

(73) Assignee: Navix International Limited, Road Town (VG)

( * ) Notice: Subject to any disclaimer, the term of this patent is extended or adjusted under 35 U.S.C. 154(b) by 859 days.

This patent is subject to a terminal disclaimer.

(21) Appl. No.: 16/403,653

(22) Filed: May 6, 2019

(65) Prior Publication Data

US 2019/0254564 A1    Aug. 22, 2019

Related U.S. Application Data

(63) Continuation of application No. 15/572,815, filed as application No. PCT/IB2016/052687 on May 11, 2016, now Pat. No. 10,278,616.

(Continued)

(51) Int. Cl.
*A61B 5/06* (2006.01)
*A61B 6/03* (2006.01)
(Continued)

(52) U.S. Cl.
CPC ............ *A61B 5/066* (2013.01); *A61B 5/0538* (2013.01); *A61B 5/063* (2013.01); *A61B 5/068* (2013.01);
(Continued)

(58) Field of Classification Search
CPC ......... A61B 5/066; A61B 24/00; A61B 24/10; A61B 24/20; A61B 5/0422; A61B 5/044;
(Continued)

(56) References Cited

U.S. PATENT DOCUMENTS 5,634,469 A   6/1997 Bruder et al.
5,697,377 A   12/1997 Wittkampf
(Continued)

FOREIGN PATENT DOCUMENTS

EP      1504713           2/2005
WO    WO 2007/042986    4/2007
(Continued)

OTHER PUBLICATIONS

Communication Relating to the Results of the Partial International Search dated Aug. 26, 2016 From the International Searching Authority Re. Application No. PCT/IB2016/052687.
(Continued)

*Primary Examiner* — Eun Hwa Kim

(57) ABSTRACT

There is provided a computerized method of tracking a position of an intra-body catheter, comprising: physically tracking coordinates of the position of a distal portion of a physical catheter within the physical body portion of the patient according to physically applied plurality of electrical fields within the body portion and measurements of the plurality of electrical fields performed by a plurality of physical electrodes at a distal portion of the physical catheter; registering the physically tracked coordinates with simulated coordinates generated according to a simulation of a simulated catheter within a simulation of the body of the patient, to identify differences between physically tracked location coordinates and the simulation coordinates; correcting the physically tracked location coordinates according to the registered simulation coordinates; and providing the
(Continued)

corrected physically tracked location coordinates for presentation.

32 Claims, 14 Drawing Sheets

Related U.S. Application Data

(60) Provisional application No. 62/304,455, filed on Mar. 7, 2016, provisional application No. 62/291,065, filed on Feb. 4, 2016, provisional application No. 62/160,080, filed on May 12, 2015.

(51) Int. Cl.
| | |
|---|---|
| *A61B 34/20* | (2016.01) |
| *A61B 18/14* | (2006.01) |
| *A61B 5/0538* | (2021.01) |
| *A61B 90/00* | (2016.01) |
| *A61B 34/10* | (2016.01) |
| *G16H 50/50* | (2018.01) |
| *G16H 10/60* | (2018.01) |
| *G16H 30/20* | (2018.01) |
| *A61B 5/287* | (2021.01) |
| *A61B 5/339* | (2021.01) |
| *A61B 18/00* | (2006.01) |
| *A61B 5/055* | (2006.01) |
| *A61M 25/01* | (2006.01) |
| *A61B 17/00* | (2006.01) |

(52) U.S. Cl.
CPC .............. *A61B 5/287* (2021.01); *A61B 5/339* (2021.01); *A61B 6/032* (2013.01); *A61B 18/1492* (2013.01); *A61B 34/10* (2016.02); *A61B 34/20* (2016.02); *A61B 90/37* (2016.02); *G16H 10/60* (2018.01); *G16H 30/20* (2018.01); *G16H 50/50* (2018.01); *A61B 5/055* (2013.01); *A61B 90/39* (2016.02); *A61B 2017/00026* (2013.01); *A61B 2018/00351* (2013.01); *A61B 2018/00357* (2013.01); *A61B 2018/00577* (2013.01); *A61B 2018/00642* (2013.01); *A61B 2018/00702* (2013.01); *A61B 2018/00738* (2013.01); *A61B 2018/00761* (2013.01); *A61B 2018/00791* (2013.01); *A61B 2018/00875* (2013.01); *A61B 2018/00904* (2013.01); *A61B 2034/102* (2016.02); *A61B 2034/104* (2016.02); *A61B 2034/105* (2016.02); *A61B 2034/107* (2016.02); *A61B 2034/2046* (2016.02); *A61B 2034/2053* (2016.02); *A61B 2034/2065* (2016.02); *A61B 2090/065* (2016.02); *A61B 2090/365* (2016.02); *A61B 2090/374* (2016.02); *A61B 2090/3762* (2016.02); *A61B 2090/3983* (2016.02); *A61B 2562/0209* (2013.01); *A61M 2025/0166* (2013.01)

(58) Field of Classification Search
CPC ....... A61B 5/0538; A61B 5/055; A61B 5/063; A61B 5/068; A61B 6/032; A61B 2017/00026; A61B 2018/00357; A61B 2018/00702; A61B 2018/00875; A61B 2018/00642; A61B 2018/00738; A61B 2018/00577; A61B 2018/00351; A61B 90/29; A61B 2090/065; A61B 90/37; A61B 90/39
See application file for complete search history.

(56) References Cited

U.S. PATENT DOCUMENTS

| | | |
|---|---|---|
| 5,983,126 A | 11/1999 | Wittkampf |
| 6,010,500 A | 1/2000 | Sherman et al. |
| 6,064,904 A | 5/2000 | Yanof et al. |
| 2002/0137014 A1 | 9/2002 | Anderson et al. |
| 2004/0097806 A1 | 5/2004 | Hunter et al. |
| 2005/0182319 A1 | 8/2005 | Glossop |
| 2006/0079759 A1 | 4/2006 | Vaillant et al. |
| 2006/0241401 A1 | 10/2006 | Govari et al. |
| 2006/0253116 A1 | 11/2006 | Avitall et al. |
| 2007/0066889 A1 | 3/2007 | Boese et al. |
| 2007/0232886 A1 | 10/2007 | Camus et al. |
| 2008/0139930 A1 | 6/2008 | Weese et al. |
| 2008/0190438 A1 | 8/2008 | Harlev et al. |
| 2008/0294034 A1 | 11/2008 | Krueger et al. |
| 2009/0221908 A1 | 9/2009 | Glossop |
| 2009/0281566 A1 | 11/2009 | Edwards et al. |
| 2010/0106154 A1 | 4/2010 | Harlev et al. |
| 2010/0283484 A1 | 11/2010 | Cohen et al. |
| 2011/0230758 A1 | 9/2011 | Eichler |
| 2012/0059249 A1 | 3/2012 | Verard et al. |
| 2012/0070046 A1 | 3/2012 | Wu et al. |
| 2012/0109115 A1 | 5/2012 | Condie et al. |
| 2012/0197243 A1 | 8/2012 | Sherman et al. |
| 2013/0079628 A1 | 3/2013 | Groszmann et al. |
| 2013/0245429 A1 | 9/2013 | Zhang et al. |
| 2014/0187949 A1 | 7/2014 | Zhao et al. |
| 2015/0320515 A1 | 11/2015 | Edwards et al. |
| 2018/0153437 A1 | 6/2018 | Schwartz et al. |
| 2018/0240237 A1 | 8/2018 | Donhowe et al. |
| 2019/0307514 A1 | 10/2019 | Schwartz et al. |

FOREIGN PATENT DOCUMENTS

| | | |
|---|---|---|
| WO | WO 2014/091418 | 6/2014 |
| WO | WO 2016/181316 | 11/2016 |
| WO | WO 2018/011757 | 1/2018 |
| WO | WO 2018/011757 A9 | 1/2018 |

OTHER PUBLICATIONS

International Preliminary Report on Patentability dated Nov. 23, 2017 From the International Bureau of WIPO Re. Application No. PCT/IB2016/052687. (10 Pages).
International Preliminary Report on Patentability dated Jan. 24, 2019 From the International Bureau of WIPO Re. Application No. PCT/IB2017/054263. (8 Pages).
International Search Report and the Written Opinion dated Oct. 16, 2017 From the International Searching Authority Re. Application No. PCT/IB2017/054263. (16 Pages).
International Search Report and the Written Opinion dated Oct. 21, 2016 From the International Searching Authority Re. Application No. PCT/IB2016/052687. (16 Pages).
Notice Of Allowance dated Dec. 26, 2018 From the Re. U.S. Appl. No. 15/572,815. (8 pages).
Official Action dated Aug. 30, 2018 From the Re. U.S. Appl. No. 15/572,815. (22 pages).
Wittkampf et al. "LocaLisa: New Technique for Real-Time 3-Dimensional Localization of Regular Intracardiac Electrodes", Circulation, 99(10): 1312-1317, Mar. 16, 1999.
Notice of Allowance dated Feb. 8, 2022 from Re. U.S. Appl. No. 17/317,548. (8 pages).
Official Action dated Aug. 13, 2021 together with Third-Party Submission under 37 CFR 1.290 From the Re. U.S. Appl. No. 16/317,548. (39 Pages).
Notification Regarding Third-Party Preissuance Submission dated Jan. 29, 2021 From the Re. U.S. Appl. No. 16/317,548.(2 Pages).
Third Party IDS Submission under 37 CFR 1.290 filed on Jan. 29, 2021 From the Re. U.S. Appl. No. 16/317,548.(2 Pages).

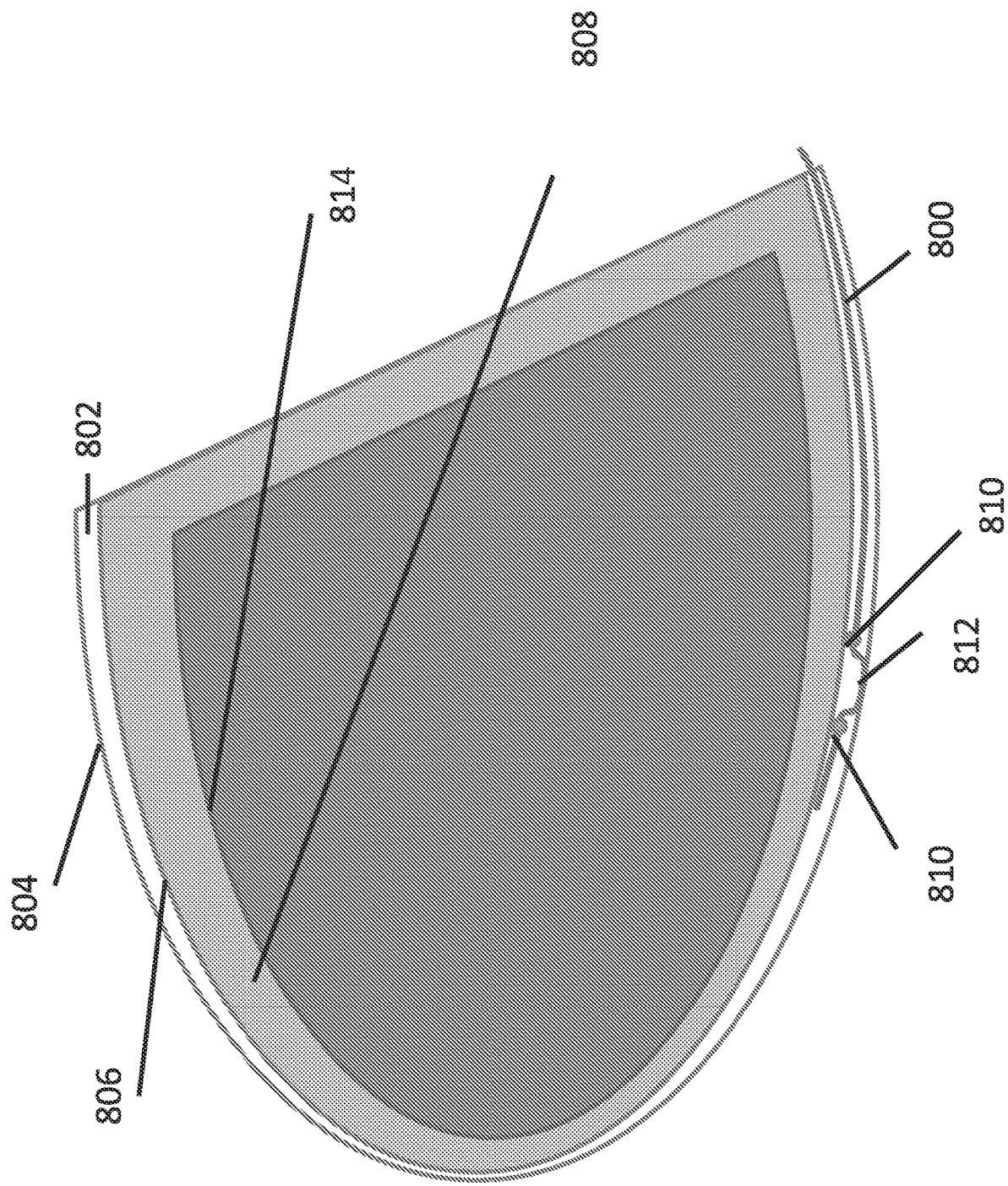

SYSTEMS AND METHODS FOR TRACKING AN INTRABODY CATHETER

RELATED APPLICATIONS

This application is continuation of U.S. patent application Ser. No. 15/572,815 filed on Nov. 9, 2017, which is a National Phase of PCT Patent Application No. PCT/IB2016/052687 having International Filing Date of May 11, 2016, which claims the benefit of priority under 35 USC § 119(e) of U.S. Provisional Patent Application Nos. 62/304,455 filed on Mar. 7, 2016, 62/291,065 filed on Feb. 4, 2016, and 62/160,080 filed on May 12, 2015. The contents of the above applications are all incorporated by reference as if fully set forth herein in their entirety

FIELD AND BACKGROUND OF THE INVENTION

The present invention, in some embodiments thereof, relates to systems and methods for tracking intrabody catheters and, more particularly, but not exclusively, to systems and methods for non-fluoroscopic tracking of intrabody catheters.

Systems and methods have been developed for non-fluoroscopic tracking of intrabody catheters, for example, for tracking a catheter during a cardiac procedure, such as intra-cardiac ablation.

Frederik H. M. Wittkampf, in U.S. Pat. No. 5,983,126 describes "A system and method are provided for catheter location mapping, and related procedures. Three substantially orthogonal alternating signals are applied through the patient, directed substantially toward the area of interest to be mapped, such as patient's heart. The currents are preferably constant current pulses, of a frequency and magnitude to avoid disruption with ECG recordings. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonal applied current signals. Three processing channels are used to separate out the three components as x, y and z signals, from which calculations are made for determination of the three-dimensional location of the catheter tip within the body."

SUMMARY OF THE INVENTION

According to an aspect of some embodiments of the present invention there is provided a computerized method of tracking a position of an intra-body catheter, comprising: physically tracking coordinates of the position of a distal portion of a physical catheter within the physical body portion of the patient according to physically applied plurality of electrical fields within the body portion and measurements of the plurality of electrical fields performed by a plurality of physical electrodes at a distal portion of the physical catheter; registering the physically tracked coordinates with simulated coordinates generated according to a simulation of a simulated catheter within a simulation of the body of the patient, to identify differences between physically tracked location coordinates and the simulation coordinates; correcting the physically tracked location coordinates according to the registered simulation coordinates; and providing the corrected physically tracked location coordinates for presentation.

Optionally, the method further comprises providing a dataset of a body portion of a patient including anatomical imaging data of the patient, and at least one dielectric parameter value corresponding to one or more of different tissues of the anatomical imaging data, wherein the at least one dielectric parameter value represents an initial estimated value; and generating the simulation that tracks coordinates of a position of the simulated catheter within the dataset representing the body portion according to simulated application of a plurality of electrical fields within the body portion and measurements of the plurality of electrical fields performed by a plurality of electrodes at a distal portion of the catheter. Optionally, the at least one dielectric parameter value includes an impedance value of the respective tissue. Optionally, the dataset includes at least one thermal parameter corresponding to the one or more of different tissues of the anatomical imaging data, wherein the at least one thermal parameter value affects the at least one dielectric parameter value, and wherein generating comprises generating the simulation according to simulated values of the at least one thermal parameter.

Optionally, the simulation includes a simulation of a plurality of extra-body electrodes that generate the plurality of electrical fields. Optionally, the method further comprises executing the simulation by varying at least one parameter of at least one of the extra-body electrodes, estimating an inaccuracy in simulation coordinates in proximity to a target tissue, repeating the simulation and the estimating by varying at least one of parameters, and selecting the at least one varied parameter to reduce the inaccuracy. Optionally, the at least one parameter is selected from the group consisting of: extra-body electrode location, size of transmitting extra-body electrode surface area, geometry of transmitting extra-body electrode surface area, electric field strength, electric current amplitude, and frequency of electric current.

Optionally, the simulation includes a simulation of at least one parameter that modifies the measurements of the plurality of electrical fields and/or modifies a dielectric measurement of tissue, and further comprising executing the simulation by varying the at least one parameter, estimating an inaccuracy in simulation coordinates in proximity to a target tissue, repeating the simulation and the estimating by varying at least one of the at least one parameters, and selecting the at least one varied parameter to reduce the inaccuracy. Optionally, the at least one parameter is selected from the group consisting of: location of multiple catheters, effect of drugs, effect of disease, effect of pre-applied treatments, effect of mechanical force applied to tissues, effect of applying a thermal intervention, effect of transmitting signal(s) into the body, and effect of transmitting signal(s) out of the body.

Optionally, the method further comprises injecting a pre-defined signal to the plurality of extra-body electrodes that generate the plurality of electrical fields, using the injected signal to analyze the effects before, during, and/or after an ablation procedure on measurements of the plurality of electrical fields, and correcting the physically tracked location coordinates according to the analysis.

Optionally, the method further comprises executing the simulation including another simulated catheter having a plurality of electrodes at a distal portion thereof, estimating an inaccuracy in simulation coordinates in proximity to a target tissue for each simulated catheter related to cross-talk, repeating the simulation and the estimating by varying at least one of the simulated catheters, and selecting the at least one varied catheter to reduce the inaccuracy related to cross-talk.

Optionally, registering further comprises calibrating the simulation location coordinates according to a defined anatomical and physical location of the distal end portion of the physical catheter.

Optionally, the simulation includes determining for tissue being ablated according to the corrected physically tracked location coordinates, at least one of: a power loss density (PLD) pattern, a gasification transition, and a temperature pattern.

Optionally, the method further comprises receiving a real-time measurement of at least one dielectric parameter of at least one intra-body tissue; generating an updated simulation by updating the initial estimated value of the at least one dielectric parameter value with the real-time measurement; and repeating the registering and the correcting. Optionally, the registering and the correcting are repeated until a stop condition is met, wherein the stop condition is identified by matching of a predefined signal template indicative of achievement of a desired ablation pattern to sensed signals and/or measurements. Optionally, the matched predefined signal template is indicative of at least one of: tissue coagulation, tissue edema, transmural ablation, continuous ablation line, safety indicator, and procedure effectiveness indicator.

Optionally, the at least one dielectric parameter is at least one of impedance and conductivity, and the at least one intra-body tissue is at least one of blood and myocardium. Optionally, the generating, the registering, and the correcting are performed for a sub-volume that includes a target tissue in near proximity to the distal end of the physical catheter. Alternatively or additionally, the generating, the registering, and the correcting are iteratively performed with decreasing volumes of the sub-volume as the distance between the distal end of the physical catheter and the target tissue decreases. Optionally, the iterations are performed to achieve an accuracy of about +/−1 millimeter of the corrected physically tracked coordinates.

Optionally, the method further comprises measuring a thickness of a tissue including a target tissue according to a dataset including anatomical image data of the patient; iteratively receiving, from at least one electrode of the physical catheter, at least one measurement of at least one dielectric parameter of tissue in proximity to the target tissue, the at least one measurement performed before an ablation of the target tissue, during the ablation, and after the ablation; and iteratively correlating the measured thickness with the received at least one electrical parameter to estimate at least one of a lesion volume and a lesion depth.

Optionally, the simulation includes a simulated ablation of the target tissue according to a simulated optimal contact force between the distal end portion of the simulated catheter and tissue in proximity to the target tissue, and further comprising correlating the at least one dielectric parameter to estimate a quality of the contact force relative to the simulated optimal contact force. Optionally, the estimated quality of the contact force is selected from the group consisting of: suboptimal contact force, optimal contact force, and excessive contact force. Optionally, the simulation is according to at least one ablation parameter. Optionally, the at least one measurement is performed in at least two frequencies.

Optionally, the method further comprises iteratively receiving, from at least one electrode of the physical catheter during the physically tracking, at least one measurement of a dielectric parameter of tissue in proximity to a target tissue, the at least one measurement performed a plurality of locations in proximity to the target tissue; analyzing the at least measurement associated with each of the plurality of locations to identify an electrical tissue signature indicative of at least one fibrotic tissue region; and mapping the at least one fibrotic tissue region to a dataset including anatomical image data of the patient, for display.

Optionally, the method further comprises analyzing a trajectory of the physically tracked coordinates of the position of a distal portion of a physical catheter over a time range including at least one cardiac cycle; and estimating a quality of contact between the distal portion of the physical catheter and a pulsating tissue portion according to the analyzed trajectory. Optionally, analyzing further comprises at least one of measuring and simulating motion of the pulsating tissue over the time range; and correlating the physically tracked coordinates of the position of the distal portion with the motion of the pulsating tissue. Optionally, measuring of the pulsating tissue is performed according to gating of a real-time ECG measurement.

Optionally, the body portion includes a heart and the simulation includes tracking coordinates of navigation of the simulated catheter within the heart for an intra-cardiac ablation procedure.

Optionally, the physically tracking is based on impedance based mapping techniques.

Optionally, the method further comprises receiving, from at least one electrode of the physical catheter contacting a tissue during the physically tracking, at least one measurement of a dielectric parameter of tissue in proximity to a target tissue; applying a trained machine learning method to the at least one measurement to generate a correlated estimated applied force between the physical catheter and the contacting tissue; wherein the trained machine learning method is based on a fitted correlation between multiple impedance values measured at multiple locations of a sample tissue similar to the contacting tissue. Optionally, the estimated applied contact force is selected from the group consisting of: suboptimal contact force, optimal contact force, and excessive contact force.

According to an aspect of some embodiments of the present invention there is provided a system for tracking a position of an intra-body catheter, comprising: an output interface for communicating with a display; an electrode interface for communicating with a plurality of physical electrodes on a distal end portion of a physical catheter designed for intra-body navigation; a program store storing code; and a processor coupled to the output interface, the electrode interface, and the program store for implementing the stored code, the code comprising: code to receive measurements of a plurality of electrical fields applied within the body portion, measured by the plurality of physical electrodes; code to calculate and physically track coordinates of the position of the distal end of the physical catheter within the physical body portion of the patient; code to register the physically tracked coordinates with simulation coordinates generated according to a simulation of a simulated catheter within a simulation of the body of the patient, to identify differences between physically tracked location coordinates and the simulation coordinates; code to correct the physically tracked location coordinates obtained according to the simulation coordinates; and code to transmit the corrected physically tracked location coordinates to the output interface.

Optionally, the system further comprises an imaging interface for communicating with an imaging modality that acquires a dataset of anatomical imaging data of a patient; wherein the processor is further coupled to the imaging interface; code to receive the dataset, and associate at least one dielectric parameter value corresponding to different tissues of the anatomical imaging data of the dataset, wherein the at least one dielectric parameter value represents an initial estimated value; and code to generate the simulation that tracks coordinates of a position of the simulated catheter within the dataset representing the body portion according to simulated application of a plurality of electrical fields within the body portion and measurements of the electrical field performed by a plurality of electrodes at a distal portion of the catheter. Optionally, the dataset includes three dimensional (3D) anatomical imaging data acquired by at least one of a CT and an MRI. Optionally, the corrected physically tracked location coordinates are displayed within a presentation of the dataset.

Optionally, the system further comprises a connector having a first port for connecting to the physical catheter, a second port for connecting to a control unit associated with the physical catheter, and a third port for connecting to the electrode interface, the connector including circuitry to intercept signal transmission between the physical catheter and the control unit and transmit the intercepted signals to the electrode interface without interfering with the signal transmission between the physical catheter and the control unit.

According to an aspect of some embodiments of the present invention there is provided a catheter for insertion into a pericardial space and measuring a dielectric property of a portion of a myocardium within the pericardial space, comprising: a plurality of sensors spaced apart and disposed at a distal end portion of a catheter, the plurality of sensors arranged to contact a visceral pericardium in contact with a myocardium of a heart, the plurality of sensors arranged to measure at least one dielectric property of a portion of a myocardium; and an isolation element disposed at a distal end portion of a catheter, the isolation element arranged to physically isolate a region of a parietal pericardium from contact with a region of the visceral pericardium between the plurality of sensors in contact with the visceral pericardium; wherein the distal end portion of the catheter is adapted for expansion within the pericardial space, from a first contracted stated wherein the distal end portion of the catheter is sized for insertion a pericardial space, to a second expanded state, wherein during the expanded state the plurality of sensors contact the visceral pericardium and the isolation element physically isolates the region between the sensors from the parietal pericardium.

Optionally, the isolation element is arranged to apply a contact force between the plurality of sensors and the visceral pericardium.

Optionally, the plurality of sensors are in communication with an interface of a unit, the unit comprising: a sensor interface for communicating with the plurality of sensors; a program store storing code; and a processor coupled to the sensor interface, and the program store for implementing the stored code, the code comprising: code to receive signals from the plurality of sensors and calculate an impedance of the myocardium.

Optionally, the isolation element is a strut arranged in a U shape in the expanded state, wherein the plurality of sensors are disposed on the distal arms of the U, and the arc of the U is arranged to urge the parietal pericardium away from the visceral pericardium to form the isolated region.

Optionally, the isolation element is arranged to physically isolate a region of the parietal pericardium from contact with a region of the visceral pericardium in near proximity around the plurality of sensors in contact with the visceral pericardium.

Optionally, the sensors are designed to measure a real and imaginary impedance component substantially concomitantly at a first frequency of about 40 kHz and at a second frequency of about 1 MHz.

According to an aspect of some embodiments of the present invention there is provided a computerized method for tracking a position of an intra-body catheter, comprising: receiving location coordinates of a catheter within a body of a patient, the location coordinates measured based on applied electric fields; and correcting the location coordinates according to a simulation of the catheter within the body based on a dielectric map including acquired anatomical imaging data of the patient and at least one dielectric parameter value corresponding to one or more different tissues identified within the anatomical imaging data.

According to an aspect of some embodiments of the present invention there is provided a system for tracking a position of an intra-body catheter, comprising: an output interface for communication with a display; an input interface for communication with a navigation system; a program store storing code; and a processor coupled to the input interface, the output interface, and the program store for implementing the stored code, the code comprising: code to receive, via the input interface, location coordinates of a catheter within a body of a patient, the location coordinates measured based on applied electric fields; code to correct the location coordinates according to a simulation of the catheter within the body based on a dielectric map including acquired anatomical imaging data of the patient and at least one dielectric parameter value corresponding to one or more different tissues identified within the anatomical imaging data; and code to provide the corrected location coordinates to the output interface for presentation on the display.

According to an aspect of some embodiments of the present invention there is provided a method for estimating contact force between an intra-body catheter and a tissue of a body of a patient, comprising: receiving, at least one impedance measurement of a tissue of a patient in contact with an intra-body catheter, the at least one impedance measurement based on a signal transmitted between at least one electrode on the intra-body catheter in contact with the tissue and at least one other electrode; analyzing the at least one impedance measurement according to a trained machine learning method that correlates the at least one impedance measurement with an estimated applied force, wherein the trained machine learning method is based on a fitted correlation between multiple impedance values measured at multiple locations of a sample tissue similar to the tissue of the body of the patient; and providing the estimated applied force for presentation to a user.

Optionally, the analyzing comprises correlating the at least one impedance measurement with an applied contact force category. Optionally, the applied contact force category is selected from the group consisting of: suboptimal contact force, optimal contact force, and excessive contact force.

According to an aspect of some embodiments of the present invention there is provided a method for estimating at least one dimension of an ablated tissue lesion from at least one impedance measurement, comprising: receiving, at least one impedance measurement of a tissue of a patient in contact with an intra-body catheter, the at least one impedance measurement based on a signal transmitted between at least one electrode on the intra-body catheter in contact with the tissue and at least one other electrode; analyzing the at least one impedance measurement according to a trained machine learning method that correlates the at least one impedance measurement with at least one estimated dimension of the ablated tissue, wherein the trained machine learning method is based on a fitted correlation between multiple dimensions measured at multiple locations of a sample tissue similar to the tissue of the body of the patient; and providing the estimated at least one dimension for presentation to a user.

Optionally, the at least one impedance measurement of the tissue is received at least one of: before an ablation of the tissue and after the ablation of the tissue.

Optionally, the at least one dimension is selected from the group consisting of: depth, surface diameter, and volume.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions.

Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 8A is a schematic of a catheter for measuring one or more dielectric properties of the myocardium from within the pericardial space which may be used with the method of FIG. 1 and/or system of FIG. 2, in accordance with some embodiments of the present invention;

Figure 13A:
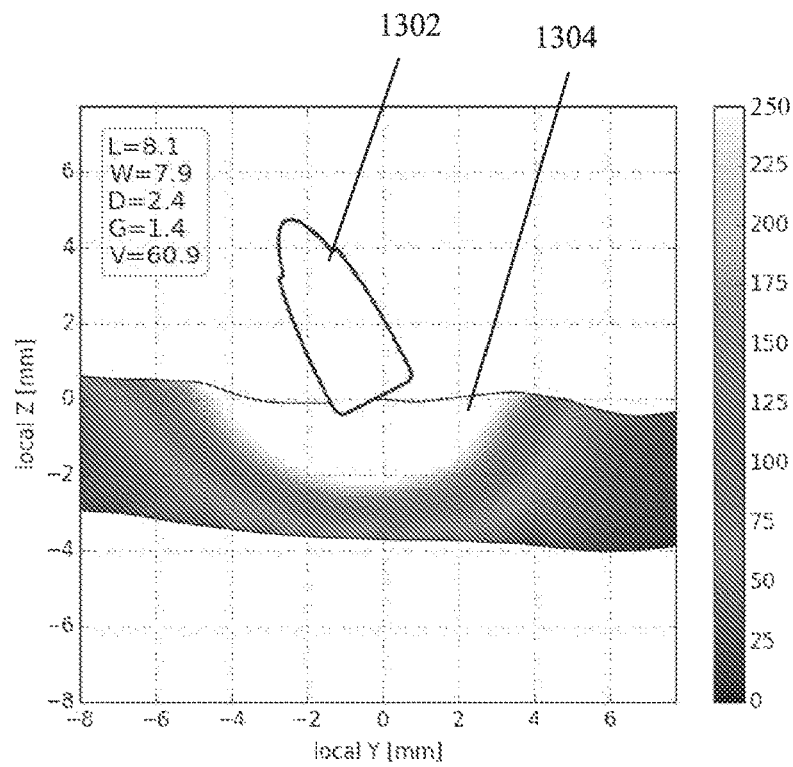
Figure 13B:
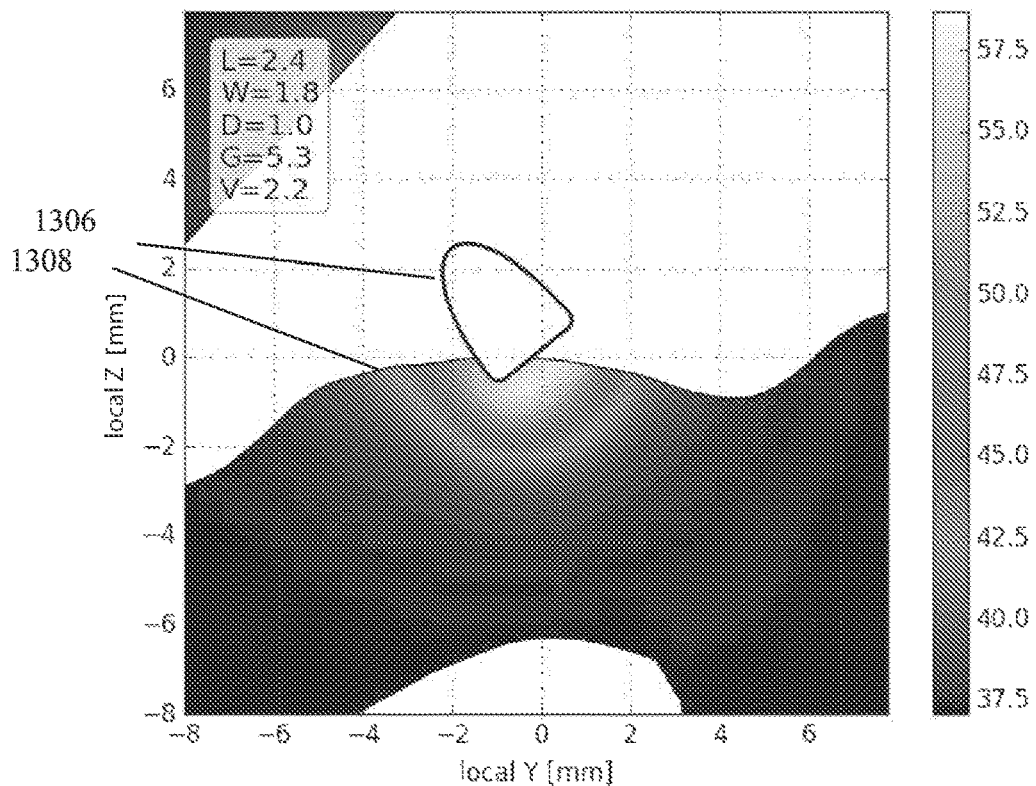

FIG. 13A is a graph depicting the calculated PLD pattern created by an electrode (e.g., RF ablation electrode(s)) in a tissue, in accordance with some embodiments of the present invention; and FIG. 13B is a graph depicting the calculated temperature pattern (in degrees Celsius) created by an electrode (e.g., RF ablation electrode(s)) in a tissue, in accordance with some embodiments of the present invention.

DESCRIPTION OF SPECIFIC EMBODIMENTS OF THE INVENTION

The present invention, in some embodiments thereof, relates to systems and methods for tracking intrabody catheters and, more particularly, but not exclusively, to systems and methods for non-fluoroscopic tracking of intrabody catheters.

One form of catheter ablation known as RF ablation relies heating caused by the interaction between a high-frequency alternating current (e.g., 350-500 kilohertz ((kHz)) introduced to a treatment region, and dielectric properties of material (e.g., tissue) in the treatment region. One variable affecting the heating is the frequency-dependent relative permittivity κ of the tissue being treated. The (unitless) relative permittivity of a material (herein, κ or dielectric constant) is a measure of how the material acts to reduce an electrical field imposed across it (storing and/or dissipating its energy). Relative permittivity is commonly expressed as $$\kappa = \varepsilon_r(\omega) = \frac{\varepsilon(\omega)}{\varepsilon_o},$$

where $\omega=2\pi f$, and f is the frequency (of an imposed signal, for example, voltage). In general, $\varepsilon_r(\omega)$ is complex valued; that is: $\varepsilon_r(\omega)=\varepsilon'_r(\omega)+i\varepsilon''_r(\omega)$.

The real part $\varepsilon'_r(\omega)$ is a measure of energy stored in the material (at a given electrical field frequency and/or voltage and/or amplitude), while the imaginary part $\varepsilon''_r(\omega)$ is a measure of energy dissipated. It is this dissipated energy that is converted, for example, into heat for ablation. Loss in turn is optionally expressed as a sum of dielectric loss $\varepsilon''_{rd}$ and conductivity σ as $$\varepsilon''_r(\omega) = \varepsilon''_{rd} + \frac{\sigma}{\omega \cdot \varepsilon_o}.$$

Any one of the above parameters: namely κ, ε, $\varepsilon'_r$, $\varepsilon''_r$, σ, and/or $\varepsilon''_{rd}$, may be referred to herein as a dielectric parameter (sometimes referred to herein as electric parameter). The term dielectric parameter encompasses also parameters that are directly derivable from the above-mentioned parameters, for example, loss tangent, expressed as $$\tan \sigma = \frac{\varepsilon''_r}{\varepsilon'_r},$$

complex refractive index, expressed as $n=\sqrt{\varepsilon_r}$, and impedance, expressed as $$Z(\omega) = \sqrt{\frac{i\omega}{\sigma + i\omega\varepsilon_r}} \text{ (with } i = \sqrt{-1} \text{)}.$$

Herein, a value of a dielectric parameter of a material may be referred to as a dielectric property of the material. For example, having a relative permittivity of about 100000 is a dielectric property of a 0.01M KCl solution in water at a frequency of 1 kHz, at about room temperature (20°, for example). Optionally, a dielectric property more specifically comprises a measured value of a dielectric parameter. Measured values of dielectric parameters are optionally provided relative to the characteristics (bias and/or jitter, for example) of a particular measurement circuit or system. Values provided by measurements should be understood to comprise dielectric properties, even if influenced by one or more sources of experimental error. The formulation "value of a dielectric parameter" is optionally used, for example, when a dielectric parameter is not necessarily associated with a definite material (e.g., it is a parameter that takes on a value within a data structure).

Dielectric properties as a function of frequency have been compiled for many tissues, for example, C. Gabriel and S. Gabriel: Compilation of the Dielectric Properties of Body Tissues at RF and Microwave Frequencies (web pages presently maintained at //niremf.ifac.cnr.it/docs/DIELECTRIC/home.html).

An aspect of some embodiments of the present invention relates to systems and/or methods (e.g., code) for tracking the position of a distal end portion of an intra-body catheter (e.g., tracking the position of one or more electrodes and/or sensors located on catheter, e.g., the distal end thereof), by correcting a position (e.g., coordinates) of the distal end portion measured according to one or more electrical and/or dielectric and/or thermal parameters (e.g., field, current, voltage, and/or impedance), by correlation with a simulation. The simulation may include simulated positions of a simulated intra-body catheter within an acquired anatomical imaging dataset of the patient, the dataset associated with estimated dielectric parameter values and/or with estimated thermal parameter values. The corrected position of the distal end may be displayed, for example, on a screen within the acquired anatomical image of the patient. The systems and/or methods may improve the accuracy of the position measured according to the electrical parameters and/or the thermal parameters with the correction according to the simulation. In this manner, the relatively higher accuracy may allow to perform treatment procedures that require a higher degree of accuracy in positioning of the distal end of the catheter, for example, neuromodulation and/or ablation; e.g., neuromodulation and/or ablation of ganglionic plexi (GP) or other nervous tissues (e.g., neural fibers, neural synapses, neural sub-systems, and/or organ specific nervous tissue) in the wall of the heart and/or other organs and/or tissues (e.g., carotid body, aortic arch, pulmonary, renal, splenic, hepatic, inferior mesenteric, superior mesenteric, muscular and/or, penile nervous tissue).

Optionally, the simulation is iteratively updated according to one or more parameters measured in real-time, for example, electrical parameters and/or thermal parameters of tissues by intra-body sensors, optionally dielectric parameters, such as impedance of the myocardium of the heart (or other target-related tissue), and/or conductivity of the blood, and/or thermal parameters such as thermal conductivity and/or heat capacity. The measured values may be fed back into the simulation, to update the estimated electrical values and/or thermal values with the measured parameters values. The simulation may be re-generated to generate an updated set of simulated positions for correcting the measured physical location of the distal end of the catheter. Optionally, the measuring and updating of the simulation are iterated, to improve the accuracy of the corrected distal end position. The iteration may be performed to reach a target accuracy, such as an accuracy fine enough for performing the treatment procedure.

Optionally, the iterations of updating the simulation are performed on selected sub-volumes within the dataset, optionally including the target tissue and the distal end of the catheter. As the catheter is navigated towards the target tissue, the selected sub-volume may decrease. The decreased simulated volume may achieve relatively higher accuracy in the position of the distal end of the catheter. For example, as the procedure is performed, and the catheter is navigated from a vascular access point toward a target region inside a heart chamber for ablation, the simulation is updated, and the accuracy of the position of the catheter distal end increases, until the highest accuracy is reached when the distal end is in close proximity to the target tissue.

Optionally, the simulation tracks the position of the simulated distal end of the catheter during a simulation of the prospective procedure, for example, intra-cardiac ablation. The simulation may estimate the position of the simulated distal end according to simulated measurements performed by simulated electrodes at the simulated distal end of simulated electric parameters generated by multiple extra-body positioned electrodes (e.g., on the skin of the simulated patient).

Optionally, one or more parameters of the simulation are adjusted in a pre-planning phase, which may be performed off-line, before the patient undergoes the procedure. The error in accuracy (and/or absolute accuracy) of calculating the location of the distal end may be estimated for each adjusted parameter. The parameter that is associated with the relatively lowest error in accuracy and/or relatively highest accuracy may be selected. The pre-planning phase may select the adjusted parameters before the patient undergoes the procedure, for use during the procedure. The parameters selected in the pre-planning phase may be related to the extra-body electrodes, for example, to select the extra-body electrodes and/or position of the extra-body electrodes in advance, for use during the procedure. The simulation may select the parameters to achieve the lowest error and/or highest accuracy. The simulated parameters may alter the measurements of the electric field measured by the sensors at the distal end of the catheter and/or alter dielectric and/or thermal measurements of tissues, by altering the electric and/or thermal parameters of tissues. The alternation of the electric field measurements by the parameter(s) may introduce error into determination of the coordinates representing the location of the catheter using the electric field. The simulation of the parameters helps determine the actual location of the catheter, by determining the required correction of the measurements according to the simulation. The parameters may relate to one or more additional catheters that are used in the procedure being simulated. The parameters may be related to the cross-talk caused by the one or more additional catheters with the original catheter. The simulation may select one or both of the catheters (e.g., from commercially available catheters) to reduce cross-talk, which may reduce the error and/or improve accuracy of detecting the position. Alternatively or additionally, the parameters may be related to simulating the effect of drugs, for example, the estimated effect on ionic concentration in the body resulting from the drugs, which affects the electrical parameters. Alternatively or additionally, the parameters may be related to simulating the effects of disease, for example, reduced elasticity in the vasculature due to an existing medical condition, or the presence of tumors in body organs. Alternatively or additionally, the parameters may be related to simulating the effects of the treatment being planned, to help determine whether the treatment will help the patient or not. Alternatively or additionally, the parameters may be related to simulating the effect of mechanical force, for example, the effect of puncturing the heart septum for access from one atrium to another. Alternatively or additionally, the parameters may be related to simulating the effects of delivering thermal intervention, such as hyperthermia, or freezing, for example, by simulating the temperature effects on the tissue and/or resulting effects on electrical values. Alternatively or additionally, the parameters may be related to simulating the effects of transmitting signal(s) into the body from outside the body, for example, the effects of the signal on the electrical and/or thermal parameters of the tissues. Alternatively or additionally, the parameters may be related to simulating the effects of transmitting signal(s) to the outside of the body from inside the body, for example, the effects of the signal on the electrical and/or thermal parameters of the tissues. Alternatively or additionally, the simulation is updated in real-time, based on real-time measurements (e.g., impedance measurements) obtained during the procedure, as described herein. The parameters may improve accuracy of the generated simulation, by considering one or more real-time parameters that may occur during the procedure, and the way in which those parameters affect the electric and/or thermal properties of the tissues.

Optionally, the simulation includes a simulation of ablation of target tissue within the acquired dataset correlated with one or more estimated electric and/or thermal parameters of the ablated tissue (and/or nearby tissue). The simulation may include the progression of the ablation lesion over time, correlated with contact force, tissue dielectric parameters (e.g., impedance), tissue thermal parameters, and/or other values. The simulated ablation may be used for lesion assessment based on real-time dielectric measurements (e.g., impedance) and/or thermal measurements of tissues. The simulation may include a correlation between the one or more estimated electric and/or thermal parameters and progress of the ablation, such as the size, volume, and/or depth of the ablated tissue. The simulation may include a correlation of the quality of contact between the distal end of the catheter and the tissue (i.e., the target tissue and/or nearby tissue), with the electrical and/or thermal parameters of the tissue. In this manner, real-time measurement of the dielectric and/or thermal parameters of the tissues (e.g., impedance measures of the tissues using electrodes of the distal end) may be correlated with the quality of contact (which may be presented to the operator). The quality of contact may be estimated based on machine learning methods applied to pre-acquired data (e.g., empirical data and/or calculated values). Alternatively or additionally, the real-time measurements of the dielectric and/or thermal parameters may be correlated with the simulated ablation, to provide an estimated assessment of the lesion progress. The lesion assessment may be estimated based on machine learning methods applied to pre-acquired data (e.g., empirical data and/or calculated values).

The operator, in response to the presentation, may adjust the contact (e.g., higher force or less force) to try and obtain optimal contact. The quality of contact may be correlated with the volume and/or depth of the ablation lesion, for example, the volume and/or depth of the lesion may be estimated for good quality contact. In this manner, the absolute contact force to achieve the ablation (e.g., in grams) does not need to necessarily be measured and/or estimated, instead, being estimated according to the measured electrical and/or thermal parameter. As such, the contact force may be classified, for example, into three categories: good contact (e.g., for ablation), suboptimal contact (e.g., more force needed), and excessive contact (e.g., reduction in force needed), which may be more clinically relevant to the physician than an absolute value of the measured contact force.

Alternatively or additionally, a trajectory of the motion of the distal end (e.g., due to pulsatile motion related to heart contractions) is analyzed to estimate the quality of the contact force. The trajectory of the motion of the distal end may be correlated with a simulated trajectory of the motion of the tissue in contact with the distal end, which moves due to the heart contractions. The trajectory of the motion may be correlated with other data representing heart contractions, for example, an electrocardiogram (ECG). The quality of contact may be estimated based on the correlation, for example, a high correlation represents good quality contact, and a poor correlation represents poor quality contact.

Optionally, multiple real-time measurements of electric and/or thermal parameters (e.g., impedance measurements by electrodes on the distal end of the catheter, and/or thermal conductivity, and/or heat capacity) of tissues, each performed at a different location of the distal end, are analyzed to identify electrical and/or thermal tissue signature(s) indicative of a region of fibrosis, for example, a scar due to a previous surgery, fibrotic tissue due to a previous ablation, and/or naturally occurring fibrotic tissue. Optionally, the phase value of the measured impedance may be used to analyze and/or identify the electrical tissue signature(s). The identified fibrotic regions may be mapped to the dataset, such as for presentation to the user. In this manner, the fibrotic regions may be visually identified by the operator, and avoided during the ablation procedure. The identified fibrotic regions map be inputted into the simulation in real-time, to update the simulation.

An aspect of some embodiments of the present invention relates to systems and methods for medical treatment and/or diagnosis using first and second information sources.

The first information source may be used for pre planning phase (e.g., for planning a treatment procedure). The first information source may include electro-magnetic (EM) simulation tool and/or thermal simulation tool. The first information source may receive a dataset of a body portion of a patient including anatomical imaging data of the patient (optionally 3D data), for example, acquired from imaging modality. Optionally, the provided imaging dataset includes associated dielectric and/or thermal parameter values. Optionally, the imaging data was acquired before the treatment procedure.

The second information source may be used in the treatment phase (e.g., based on real-time data). For example, information may be obtained during the treatment procedure. Optionally, the second information source may receive real-time measurement, e.g., real-time measurement of one or more dielectric and/or thermal parameter(s) of one or more intra-body organs being treated (e.g., a dielectric and/or thermal map(s)).

In some embodiments, information from the second information source is fed to the first information source (for example: real-time measurement of one or more dielectric and/or thermal parameter(s)). Such information from the second information source may modify the first information source output (e.g., the simulation may be updated to obtain updated simulation). Optionally, the updated simulation is more accurate than an initial simulation (e.g., simulation calculated in the pre-planning phase).

Optionally, information from the first information source may alter second information source output. For example, updated information from the first information source may be fed back to the second information source, e.g., may be used to change the thresholds used for example to judge the appropriateness of the treatment based on the real time measurements.

In yet another example, after a successful ablation of a point in an ablation line, the properties of the heart change and thus the dielectric parameter guiding the treatment in real time are different than the ones generated from first information source prior to the procedure, such changes in dielectric parameters may be inputted to the first information source for updating the simulation.

An aspect of some embodiments of the present invention relates to a catheter for insertion into narrow and/or small tissue region, for example, a collapsed region and/or a potential body space, for example, a pericardial space of a heart of a patient, a pleural space of a lung of a patient, for measuring one or more dielectric and/or thermal properties of a portion of a myocardium within the pericardial space, optionally impedance and/or conductance of the pericardium. The distal end portion of the catheter may include multiple sensors arranged to contact the visceral pericardium to measure the dielectric property and/or the thermal property. The distal end portion of the catheter may include an isolation element arranged to physically isolate a region of the parietal pericardium from contact with a region of the visceral pericardium between the sensors in contact with the visceral pericardium, optionally including an isolated region around the sensors. In this manner, as the sensors do not come in contact with the parietal peritoneum, the sensors measure the dielectric and/or thermal property of the myocardium while preventing or reducing errors in measurement due to interference from other nearby tissues in contact with the parietal pericardium.

An aspect of some embodiments of the present invention relates to a method for estimating contact force between an intra-body catheter and a tissue of a body of a patient, for example, to help control an ablation procedure. The method may be implemented by code stored in a program store, implementable by a processor of a computing unit (e.g., as described herein). The method may apply a trained machine learning method (e.g., statistical classifier, a fitted parametric model, one or more functions, a look-up table, support vector machine with optional radial basis functions) to correlate one or more impedance measurements (optionally measured in real-time during a procedure) with an estimated applied contact force. The impedance measurements may be performed by an electrode on the catheter contacting the tissue, to estimate the contact force between the catheter and the tissue. The impedance measurements may be performed by a plurality of electrodes. Inventors discovered that the machine learning method, trained using a set of multiple measured impedance values at different locations on similar tissue (i.e., from other patients), may correlate the real-time impedance measurement to the estimated force with sufficient accuracy to allow the operator performing the procedure to control the force application to help arrive at a desired treatment result (e.g. ablation). Inventors discovered, that even when the variability of the training set is large, the correlation between the real-time impedance measurement and applied force may be clinically significant. Optionally, the correlation is performed to an applied contact force category, which may be clinically significant (i.e., helps guide the operator to perform the desired ablation).

Optionally, the applied contact force categories include: suboptimal contact force, optimal contact force, and excessive contact force. In this manner, the operator may not necessarily be provided with the absolute force, instead, being provided with a relative measure or category that is clinically relevant to the procedure. The relative category may be more easily acted upon by the operator, for example, by increasing the force, reducing the force, or maintaining the force.

Alternatively or additionally, another trained machine learning method is applied to correlate the one or more impedance measurements with an estimated dimension or spatial data of the ablated tissue lesion, optionally one or more of: depth, surface diameter, and volume. Optionally, the real-time impedance measurements are obtained before the ablation procedure. Alternatively or additionally, the real-time impedance measurements are obtained after the ablation procedure.

The systems and/or methods described herein may provide a technical solution to the technical problem of improving navigation of a catheter within the body of a patient, and/or improving control of a catheter based ablation procedures. The location of the catheter within the body of the patient and/or the procedure being performed cannot be directly visualized. Use of X-ray based image guidance (e.g., fluoroscopy) delivers energy to the body of the patient, and is to be reduced or eliminated. Use of other navigation methods (e.g., relative to externally applied electromagnetic fields) may not be accurate enough to perform fine procedures, such as ablation.

In some embodiments, the systems and/or methods described herein may tie mathematical operations (e.g., performing calculations to generate the simulation) to the ability of a processor to execute code instructions, and to one or more sensors that measure actual data in real-time (e.g., from within the body of the patient) that is used by the processor to updated and improve the generated simulation.

In some embodiments, the systems and/or methods described herein may improve performance of computer(s) (e.g., client terminal, server), and/or networks, and/or medical imaging equipment and/or medical treatment equipment (e.g., RF catheters). For example, the improvement in accuracy obtained by updating the generated simulation using real-time measured electrical and/or thermal values (as described herein), may reduce the amount of medical imaging required (e.g., in terms of radiation dose, processing of the images, and memory to store the images) by improving the navigation and/or guidance of the catheter.

In some embodiments, the systems and/or methods described herein may create new data in the form of an updated simulation. The data of the updated simulation may be organized in a specific manner, to allow iterative updates of portions of the data according to real-time measurements.

In some embodiments, the systems and/or methods described herein may provide a unique, particular, and advanced technique of using real-time measurements to update a generated simulation, which is used in real-time to guide a catheter, for example, to navigate a catheter and/or perform a medical treatment on tissue.

Accordingly, the systems and/or methods described herein are necessarily rooted in computer technology to overcome an actual technical problem arising in guidance and/or control of instruments (e.g., catheters) within the body of a patient, for example, to perform ablation based treatment and/or navigation of the instrument.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As used herein, the term distal end is sometimes interchanged with the term catheter, for example, for tracking the position thereof. The term distal end is not meant to be necessarily limiting, serving as an example of the portion of the catheter being tracked, such as according to the location of the sensors and/or electrodes on the catheter. As such, other locations of the catheter may be tracked, and may sometimes be interchanged for the term distal end, for example, distal end portion, region away from the distal end, catheter portion, and/or other regions of the catheter.

As used herein the term ablation, for example, ablation treatment may mean application of energy by an instrument (e.g., catheter) to tissue, for example, RF, ultrasound, cryo energy (to cool the tissue), and thermal energy (to heat the tissue). The ablation is applied to attempt to reach a desired therapeutic effect, which may or may not include killing of cells.

Figure 1:
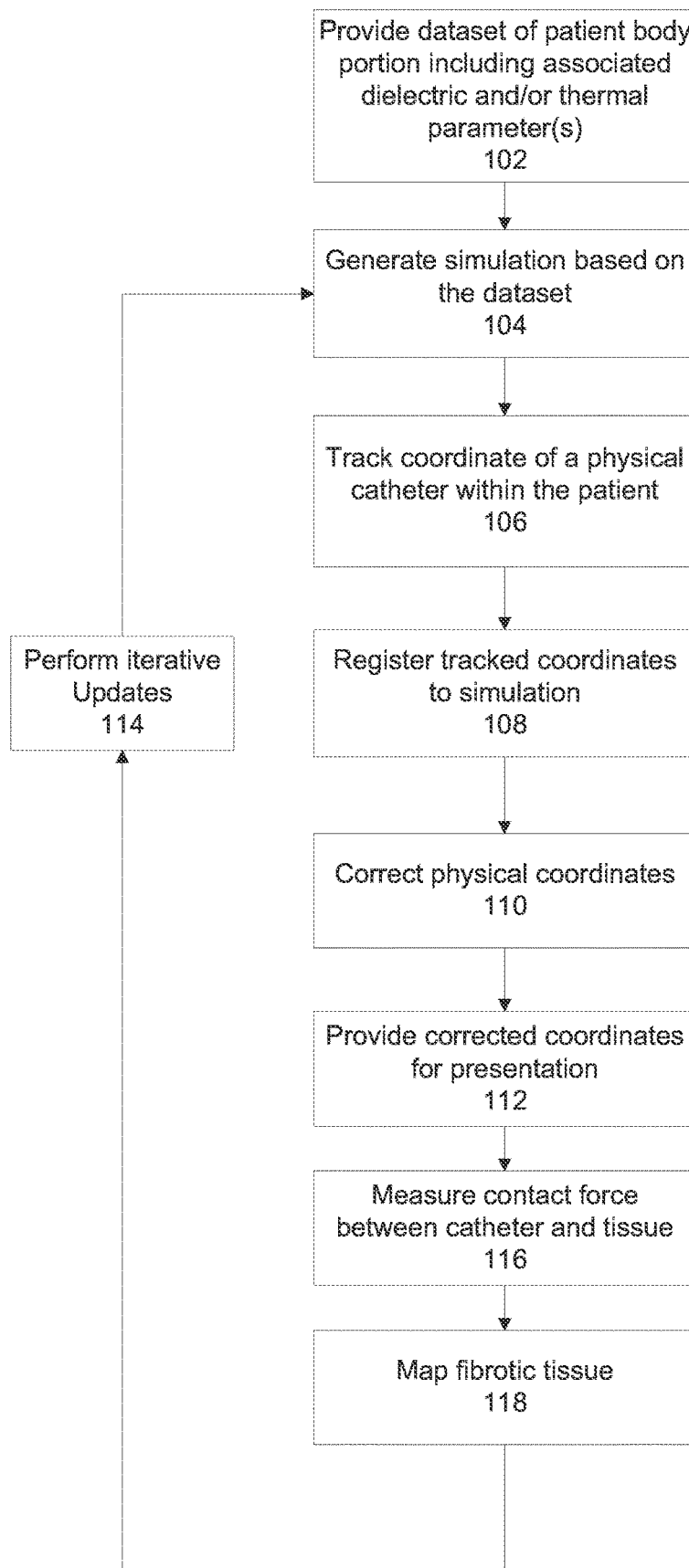
FIG. 1 is a flowchart of a method for tracking the position of an intra-body catheter, in accordance with some embodiments of the present invention.

Referring now to the drawings, FIG. 1 is a flowchart of a method for tracking the position of an intra-body catheter, in accordance with some embodiments of the present invention. The method receives a dataset representing an anatomical image (e.g., 3D CT images) of the patient, and based on dielectric properties of tissue types (e.g., impedance and/or conductivity) and/or thermal properties (e.g., thermal conductivity, heat capacity, and metabolic heat generation) identified within the anatomical image, creates a dielectric map and/or a thermal map (i.e., dataset) for the patient. The dielectric and/or thermal map is used as a basis for a generating a simulation of a simulated catheter during a simulated procedure, according to simulated positions of simulated extra-body electrodes. The output of the simulation is used to correct real-time readings of position data (e.g., of the distal end of a catheter) measured based on electric and/or thermal parameters (e.g., voltage, electric field, impedance, current).

The thermal parameters may include general thermal properties which may define living tissue and inanimate matter, for example, thermal conductivity and/or het capacity, and/or thermal properties specific to biological tissues, for example, metabolic heat generation, absorption rate, and blood perfusion rate. The thermal properties may be used as inputs into a bio heat formulation of a heat equation to estimate temperature evolution in the region of interest as a function of time and/or space.

The electric and/or dielectric parameter values may be associated with the thermal parameter values. The electric and/or dielectric properties may be temperature and/or frequency dependent. Estimation of the dielectric parameter values may be improved by simulating the thermal parameters, and/or measuring and/or calculating the thermal parameters in real time. As used herein, the term electric may mean electric and/or thermal. The term dielectric may mean dielectric and/or thermal.

Figure 2:
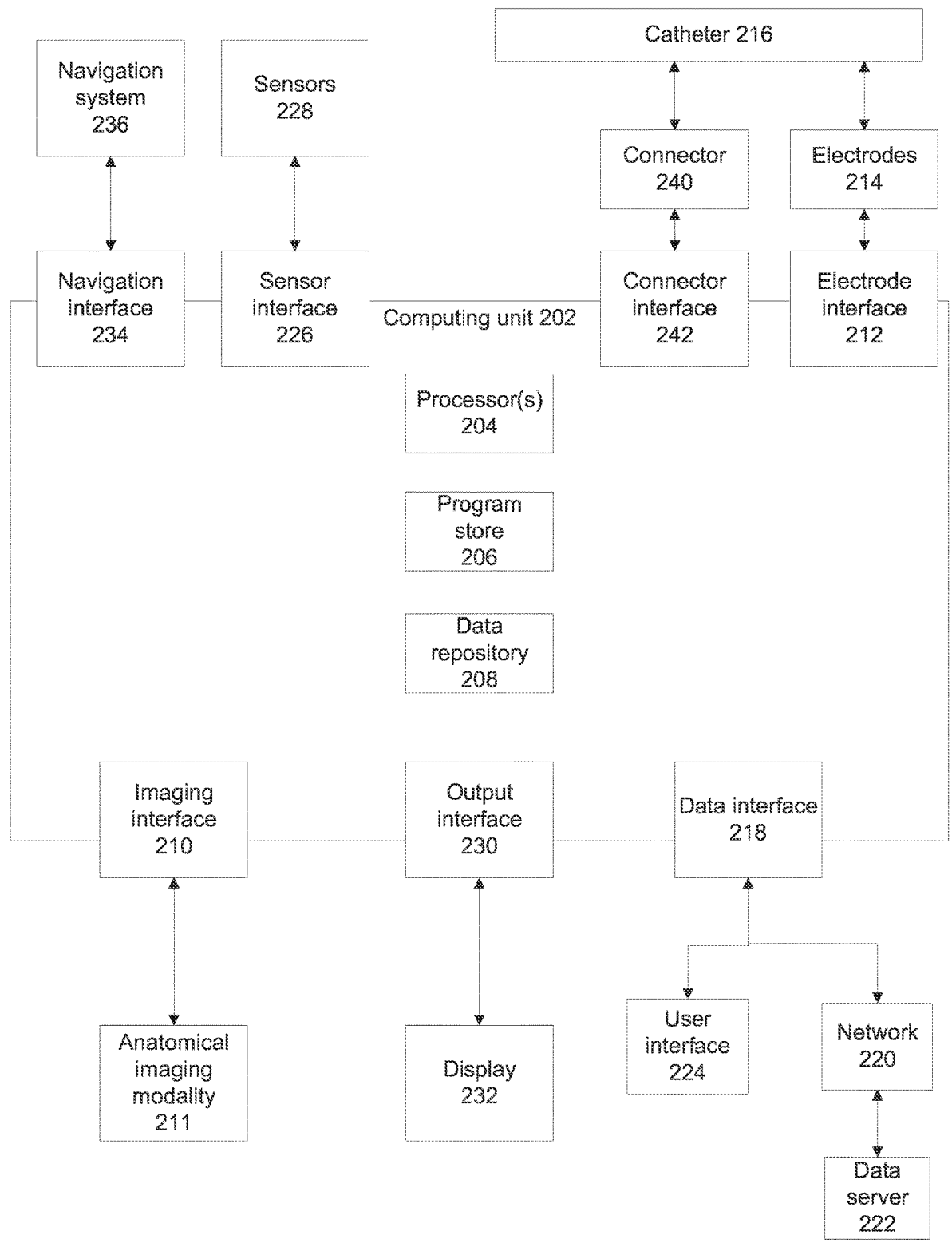
FIG. 2 is a block diagram of components of a system for tracking the position of an intra-body catheter, in accordance with some embodiments of the present invention.

The method may improve the accuracy of the original received position data. Reference is also made to FIG. 2, which is a block diagram of components of a system for tracking the position of an intra-body catheter, in accordance with some embodiments of the present invention. The system of FIG. 2 may allow for an operator to perform intra-body procedures that require relatively higher accuracy than the accuracy provided by existing electric parameter based systems, for example, radiofrequency ablation, and/or injection (e.g., chemical) based ablation, e.g., of GPs.

The method of FIG. 1 and/or system of FIG. 2 may be used to iteratively correct the location data and/or improve the accuracy of the location data by integration of real-time measurements that are used to update the simulation, for example, measurements of the impedance and/or conductance of the myocardium and/or blood and/or other tissues. The system of FIG. 2 may execute the method of FIG. 1.

It is noted that the method of FIG. 1 and/or the system of FIG. 2 may correct the location of the distal end of the catheter by separately and substantially simultaneously tracking the position of sensors, electrodes and/or other conducting ports on the distal end of the catheter. The distance between sensors on the distal end of the catheter may be used for calibration, as described herein. The location of the catheter may be derived based on the locations of the multiple sensors on the catheter's distal end.

As used herein, the terms sensor and electrode are sometimes interchangeable, for example, where referring to an element that performs measurements of one or more electrical properties (e.g., dielectric properties, conductance, impedance, voltage, current, and/or electrical field strength). For example, the electrodes may function as the sensors, such as by transmitting from one electrode to a second electrode, where the second electrode functions as a sensor. Impedance may be measured between respective electrode pairs, and/or between a designated electrode and a reference electrode (which may be located outside the body and/or within the body, such as on the catheter).

The method of FIG. 1 and/or system of FIG. 2 may provide additional features, for example, selection of the electric and/or thermal parameters (and/or elements that generate the electric and/or thermal parameters), estimation of contact force applied by the distal end of the catheter to the tissue wall, estimation of the lesion formation (e.g., size, volume and/or depth), estimation of tissue temperature, and/or mapping of fibrotic regions.

System 200 may include a program store 206 storing code (as described herein) and a processor 204 coupled to program store 206 for implementing the stored code. Optionally, more than one processor may be used. It is noted that program store 206 may be located locally and/or remotely (e.g., at a remote server and/or computing cloud), with code optionally downloaded from the remote location to the local location for local execution (or code may be entirely or partially executed remotely).

System 200 may include an imaging interface 210 for communicating with one or more anatomical imaging modalities 211 that acquire a dataset of imaging data of a patient, for example, anatomical imaging data, e.g., a computer tomography (CT) machine, an ultrasound machine (US), a nuclear magnetic resonance (NM) machine, a single photon emission computed tomography (SPECT) machine, a magnetic resonance imaging (MRI) machine, and/or other structural and/or functional anatomical imaging modality machines. Optionally, imaging modality 211 acquires three dimensional (3D) data and/or 2D data. It is noted that the anatomical images may be derived and/or acquired from functional images, for example, from functional images from an NM machine.

System 200 may include an output interface 230 for communicating with a display 232, for example, a screen or a touch screen. Optionally, the corrected physically tracked location coordinates are displayed within a presentation of the dataset, for example, the 3D acquired anatomical images are displayed on display 232, with a simulation of the location of the distal end of the catheter within the displayed image based on the corrected location.

System 200 may include an electrode interface 212 for communicating with a plurality of physical electrodes 214 and/or sensors (e.g., the electrodes may serve as the sensors) located on a distal end portion of a physical catheter 216 designed for intra-body navigation, for example, an electrophysiology (EP) ablation catheter, and/or other ablation catheter (e.g., chemical ablation or injection catheter). Alternatively or additionally, system 200 includes a navigation interface 234 for communicating with a catheter navigation system 236, optionally a non-fluoroscopic navigation system, optionally, an impedance measurement based system.

The intra-body navigation may be performed based on extra-body electrodes that receive and/or transmit current (e.g., alternating current) in different frequencies and/or different times between co-planar directions. Analysis of the electrical and/or thermal parameters obtained from the sensors of the catheter, separated into the different channels may be used to estimate the location of each sensor relative to each extra-body electrode. A calibration of the distances between the sensors (e.g., based on manufacturing specifications of the catheter, and/or measurements such as using fluoroscopy or other methods) may be performed.

Figure 8B:
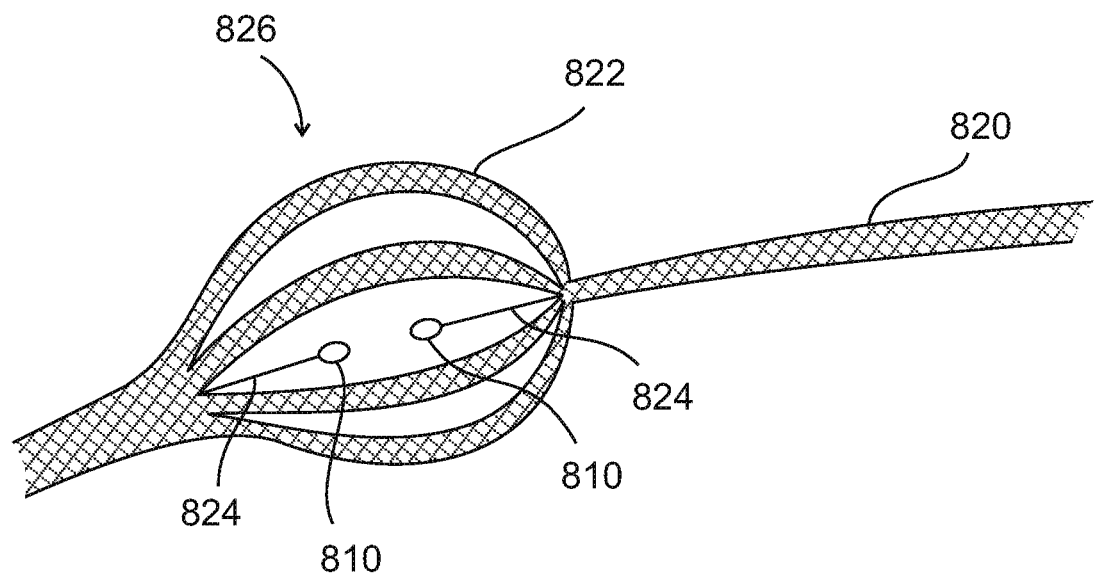
FIGS. 8B-8C are some designs of the catheter of FIG. 8A, in accordance with some embodiments of the present invention.
Figure 8C:
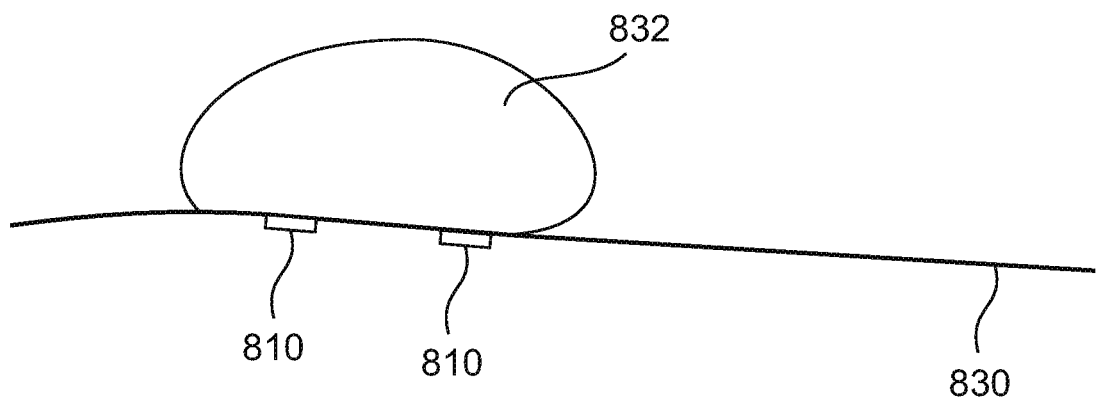

Optionally, system 200 includes a sensor interface 226 for communicating with one or more sensors 228, which may be in the body or external to the body, for example, for measuring electrical and/or thermal parameters, for example, impedance and/or conductivity and/or thermal conductivity and/or heat capacity and/or metabolic heat generation of the blood, the myocardium, and/or other tissues, for example, the catheter described herein with reference to FIGS. 8A-8C, and/or other methods described herein.

Optionally, system 200 may include a data interface 218, for communicating with a data server 222, directly or over a network 220, to acquire estimated dielectric and/or thermal tissue values for association with the acquired imaging dataset. Alternatively, the estimated dielectric and/or thermal values are stored locally, for example, on data repository 208.

Optionally, a user interface 224 is in communication with data interface 218, for example, a touch screen, a mouse, a keyboard, and/or a microphone with voice recognition software.

Optionally, system 200 (e.g., computing unit 202) includes a connector 240 connecting between catheter 216 (e.g., RF ablation catheter, injection catheter) and a connector interface 242 (and/or electrode interface 212). Connector 240 may be used to adding additional features to existing catheters, such as off the shelf catheters, for example, RF ablation catheters, at least by acting as an input of signals communicated by the catheter for processing by system 200. The signals communicated by the catheter are intercepted by circuitry within connector 240 and transmitted to interface 242 and/or 212, without interfering with the signal transmission. The intercepted signals may be analyzed by system 200, for example, to perform real-time tissue measurements (e.g., contact force, pressure, ablated volume and/or depth, temperature, and/or fibrosis mapping, as described herein), to perform localization of the catheter (e.g., as described herein), to identify the type of the catheter, and/or to identify the presence of connector 240.

Figure 9:
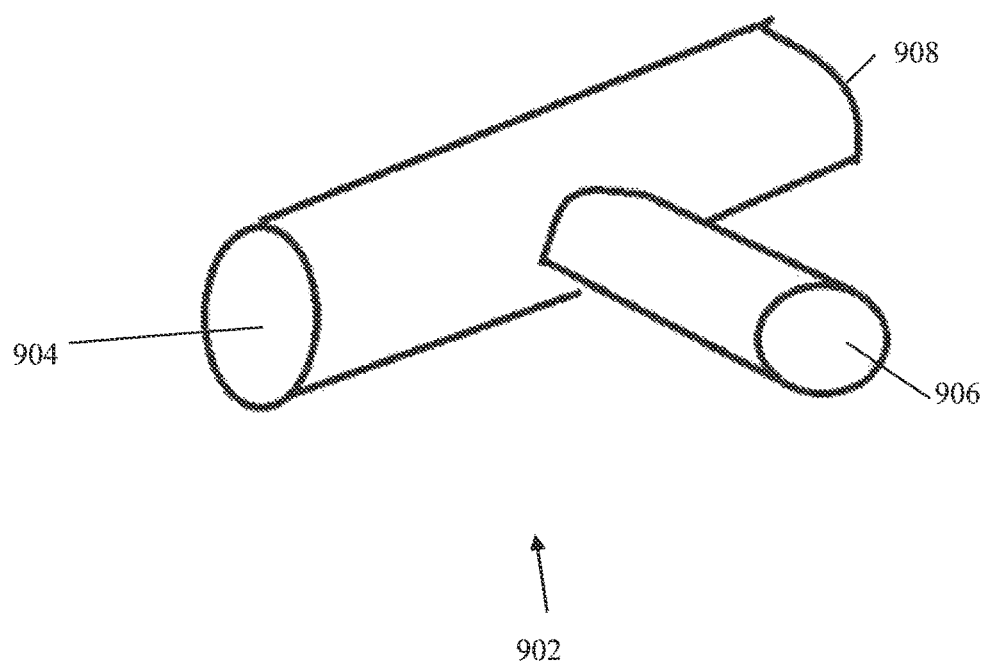
FIG. 9 is a schematic diagram of a connector for connecting a catheter to the system of FIG. 2, in accordance with some embodiments of the present invention.

Connector 240 may be implemented, for example, as shown with reference to FIG. 9, which is a schematic diagram of a connector 902 (corresponding to connector 240) for establishing communication between system 200 and a catheter, in accordance with some embodiments of the present invention. According to some embodiments, connector 902 is an element having 3 ports 904, 906, and 908 (e.g., a T shape, a Y shape, optionally having a round cross-section). Connector 902 may be designed to fit existing connectors of catheters that connect to control devices (e.g., an ablation control unit), for example, an 18 pin male to female connector. A first port 904 connects to the catheter end, a second port 908 connects to the control unit, and a third port 906 connects to connector interface 242 (or electrode interface 212) of unit 202.

Extension cables may be used to connect each respective port. Connector 902 may directly couple (e.g., plug) between the proximal end of the catheter and the respective extension cable. It is noted that the ports may be arranged in a different configuration.

Connector 902 may be designed to monitor signals between the coupled catheter and control unit, without interfering with signal transmission and/or otherwise changing the transmitted signals. Optionally, connector 902 includes pre-amplifiers for intercepted analog signals being inputted into unit 202, for example, impedance measurements, ECG, RF generator calibration, and/or vagus nerve stimulation (VNS) signals.

Optionally, connector 902 (and/or unit 202) includes circuitry and/or code implementable by a processor, to detect, test, and/or record a catheter specific feature that characterizes the coupled catheter (e.g., off-the-shelf catheter), for example, the feature is mapped to a record in a database (or look-up table or other data structure) representing data of the catheter. The coupled identified catheter may be calibrated, for example, the position of the catheter may be calibrated as described herein. Calibrated data may be stored (e.g., locally on connector 902 and/or unit 202). Data transmission between connector 902 and unit 202 may be encrypted.

Connector 902 may be designed for single use (e.g., disposable), for example, made out of relatively inexpensive materials, and/or provided sterilized.

It is noted that one or more interfaces 210, 218, 212, 226, 230, 234, 242 may be implemented, for example, as a physical interface (e.g., cable interface), and/or as a virtual interface (e.g., application programming interface). The interfaces may each be implemented separately, or multiple (e.g., a group or all) interfaces may be implemented as a single interface.

Processor 204 may be coupled to one or more of program store 206, data repository 208, and interfaces 210, 218, 212, 226, 230, 234, 242.

Optionally, system 200 includes a data repository 208, for example, for storing the dataset (e.g., imaging data of a patient), the simulation, received electrical and/or thermal parameters, and/or other data (such as: health record of a patient). The data may be displayed to a user (e.g., physician) before, during and after the procedure.

It is noted that one or more of processor 204, program store 206, data repository 208, and interfaces 210, 218, 212, 226, 230, 234, 242 may be implemented as a computing unit 202, for example, as a stand-alone computer, as a hardware card (or chip) implemented within an existing computer (e.g., catheterization laboratory computer), and/or as a computer program product loaded within the existing computer.

As described herein, program store 206 may include code implementable by processor 204 that represents a simulation tool and/or application that generates RF simulations (e.g., based on simulated generated fields) based on a provided dielectric map and/or other data.

Referring to FIG. 1, at 102, a dataset of a body portion of a patient including anatomical imaging data of the patient (optionally 3D data) is provided, for example, acquired from imaging modality 211 (e.g., CT, MRI), retrieved from repository 208, and/or acquired from an external server or other storage. Alternatively or additionally, the dataset is acquired and/or derived from a functional imaging modality, for example, NM and/or SPECT. For example, data from the NM modality may be used to infer the location of autonomous nervous system components (e.g., one or more GPs) designated for treatment on the dataset from the CT modality, for example, as described with reference to "BODY STRUCTURE IMAGING", International Publication No. WO/2014/115148 filed Jan. 24, 2014, incorporated herein by reference in its entirety.

The data obtained from the CT machine (and/or other imaging devices) may serve as a basis for geometrical structure and/or modeling of internal organs of the patient, for example, the organs are segmented using image segmentation code. The electrical and/or thermal properties and/or other values (e.g., mechanical, physiologic, other tissue related values) are associated with each organ, optionally according to the designated operational frequency used by the RF ablation catheter.

Optionally, the imaging dataset includes the target tissue for treatment in a catheterization procedure, for example, the heart. Optionally, the imaging dataset includes tissues surrounding the target tissue for simulation of the procedure, for example, a full body scan, a full thorax scan, a chest and abdominal scan, and/or a chest scan. For example, for an intra-cardiac ablation procedure, a full thorax scan may be performed.

Optionally, the imaging dataset is analyzed and/or processed to identify different types of tissues within the imaging data, for example, each pixel data or region is classified into a tissue type. Suitable classification methods include, for example, according to image segmentation methods, according to a predefined imaging atlas, and/or based on Hounsfield units.

Code stored, for example in program store 206, implementable by processor 204 accesses estimated dielectric and/or thermal parameter values, and associates each tissue type and/or pixel and/or region in the dataset with the estimated dielectric and/or thermal parameter values. Optionally, the provided imaging dataset includes the associated dielectric and/or thermal parameter values.

The dielectric and/or thermal parameter values may be obtained, for example, from a publicly available database (e.g., on data server 222), and/or calculated from a model, and/or empirically measured values from a sample of patients. It is noted that the estimated dielectric and/or thermal parameter values may reflect values that have not necessarily been measured for the patient being treated. In some embodiments, a 2D or 3D dielectric map and/or thermal map of the region (e.g., organ) or a portion of the organ is created and optionally displayed to a user.

The dataset including anatomical image data associated with the dielectric and/or thermal parameter values may sometimes be referred to herein as a dielectric map and/or thermal map. The dataset sometimes includes both the dielectric map and the thermal map. The dataset sometimes includes one of the dielectric and thermal maps. It is noted that the dielectric map may include dependencies of the dielectric parameter values on the thermal parameter values. The dielectric map information and the thermal map information may be displayed on the same map.

As used herein, the term dielectric map sometimes includes both the dielectric map and the thermal map. As used herein, the term dielectric map may sometimes be interchanged with the term thermal map.

Optionally, the anatomical image (e.g., after segmentation) and the estimated dielectric and/or thermal parameter values or the 2D or 3D dielectric map are inputted to the simulation tool, which may be implemented as code stored in program store 206 implementable by processor 204, or as a separate unit (e.g., external server, hardware card, remotely located code implementable locally).

Optionally, the dataset is used to generate a simulation as part of a pre-planning phase, for example, as described with reference to FIG. 3. The pre-planning phase simulates different parameters for the planned procedure, to help select one or more different parameters for the actual procedure, according to, for example, reduced error in tracking the location of the catheter, improved accuracy in tracking location of the catheter, selection of the treatment location of the catheter, and/or selection of ablation parameters and/or ablation lines according to a simulation of the ablation.

Ablation parameters may include one or more of: ablation power and/or duration, frequency of applied signal, angle of catheter, phase values between pairs of electrodes (e.g., when the catheter includes plurality of electrodes), electrodes to which a signal is applied, pressure applied by the catheter, order of ablation points along the ablation line and/or any other parameters that may affect the ablation procedure.

Optionally, a forecast success rate of treatment parameters (ablation parameters, treatment location, ablation method etc.) or selected catheter model(s) may be presented to the user. The user may select treatment parameters and/or catheter model(s) based on the forecast success, e.g., to obtain maximum success. For example, the catheter model(s) may be selected according to the simulation, for example, to reduce cross-talk between catheter models. In another example, the ablation location may be selected, for example, according to a simulation ablation having an estimated success rate of 85%. In yet another example, the placement of multiple catheters may be selected according to the simulation, for example, to improve the treatment of the procedure. In yet another example, the administration of drugs may be selected according to the simulation, for example, the type of saline being administered, the timing of the patient medication, and/or the administration of other drugs, for example, to improve transmission of electrical fields through the body of the patient. In yet another example, the patient's medical condition may be considered by the simulation in planning the treatment, for example, the presence of calcification deposits, tumors, or other anatomical abnormalities may be avoided or considered. In yet another example, the selection of mechanical force may be performed according to the simulation, for example, to help avoid injury to nearby tissues the applied force may be simulated. In yet another example, the selection of thermal intervention (e.g., hyperthermia, freezing) may be selected, for example, to improve treatment. In yet another example, the selection of signals transmitting into the body or out of the body may be selected, for example, the signal transmission maybe gated or synchronized with the applied RF energy and/or sensor measurements to avoid interference.

The operator may update the procedure plan according to the simulation, such as selection of a different catheter to reduce cross-talk.

Optionally, the dielectric parameters include an impedance and/or conductive value of the respective tissue and/or tissue region.

It is noted that the patient may undergo imaging before the catheterization procedure, for example, as a separate outpatient procedure.

Optionally, the dataset includes the imaging data and the one or more dielectric and/or thermal parameter values corresponding to different tissues and/or regions of the anatomical imaging data. The dielectric and/or thermal parameter value represents an initial estimated value, which may be adjusted based on real-time measurements obtained from the patient, as described herein.

Optionally, the dataset is associated with additional data, for example, mechanical parameters (e.g., fibrosis map, for example, as described with reference to block 118), physiological parameters (e.g., patient ECG patterns, patient body temperature), and other tissue specific parameters.

Optionally, the dataset is associated with additional data related to the medical state of the patient, for example, medications the patient is taking (e.g., which may affect the ionic concentration of the tissues of the patient, affecting the electrical and/or thermal parameters), the medical state of the patient (e.g., which may affect the anatomy of the patient), and a history of previous treatments (e.g., which may help predict the effects of the current treatment).

At 104, according to some embodiments, code stored in data repository 208 processes the dielectric and/or thermal map (i.e. dataset) of block 102, to generate a simulation. The simulation simulates the navigation path during the procedure or part thereof, using a simulated catheter, and simulated applied electric parameters by simulated extra-body electrodes (e.g., positioned on the skin of the patient). The simulation may be electro-magnetic (EM) simulation and/or thermal simulation.

Optionally, the simulation receives one or more of the following inputs, to generate the initial simulation and/or update the simulation (e.g., as in block 114): the anatomical model (e.g., obtained based on a CT and/or other imaging data of the patient), the dielectric map and/or thermal (initial or updated) which includes dielectric properties and/or thermal properties, fibrosis data (e.g., fibrosis map, for example, as described with reference to block 118), conductance map including acquired anatomical imaging data of the patient and at least one conductance parameter value corresponding to one or more different tissues identified within the anatomical imaging data (e.g., from a stored location based on previous conductance mapping and/or real-time mapping), ablation catheter parameters (e.g., frequency, model, type, angle of catheter), impedance measurements, thermal property measurements, and/or other data values (e.g., as described herein).

The simulation may track the position (such as coordinates) of the simulated catheter within the dataset representing the body portion according to the simulated application of the electrical fields (or other electrical parameters, such as current, impedance, and/or voltage) within the body portion (e.g., based on the extra-body simulated electrodes). The simulation may simulate the measurements of the simulated applied electrical fields, optionally as measured by electrodes at a distal portion of the simulated catheter.

Optionally, the generated simulation includes a dataset of the coordinates (or other position data) of the simulated catheter within the dataset related to navigation of the catheter as part of the procedure.

Optionally, the simulation is performed at one or more operating frequencies, for example, when simulating a catheter ablation procedure. Exemplary simulation frequencies include: about 460 kHz, about 1 megahertz (MHz), about 12.8 kHz, or other frequencies. The simulation frequency is used to measure changes during the ablation process, and correct the ablation parameters accordingly, as described herein.

Optionally, the simulation includes coordinates in space which represent a simulation of electrodes and/or sensors that provide measurements of values of the electrical and/or thermal properties. The simulation of the measured values may be used, for example to simulate the measurement of induced currents. The simulation of the induced currents may reduce the number of time the simulation is run to below the number of sampling points in space, which reduces the required computational resources to perform the simulation.

Optionally, the simulation calculates the optimal position for a multi-electrode phased RF catheter, for example, to obtain the best real-time measurements, for example, with improved signal to noise, or reduced error.

Exemplary commercially available simulation tools that may be used as a framework for generating the simulation described herein include: Sim4Life (available from Zurich Med Tech), COMSOL Multiphysics®, and CST Design Studio™.

Figure 12:
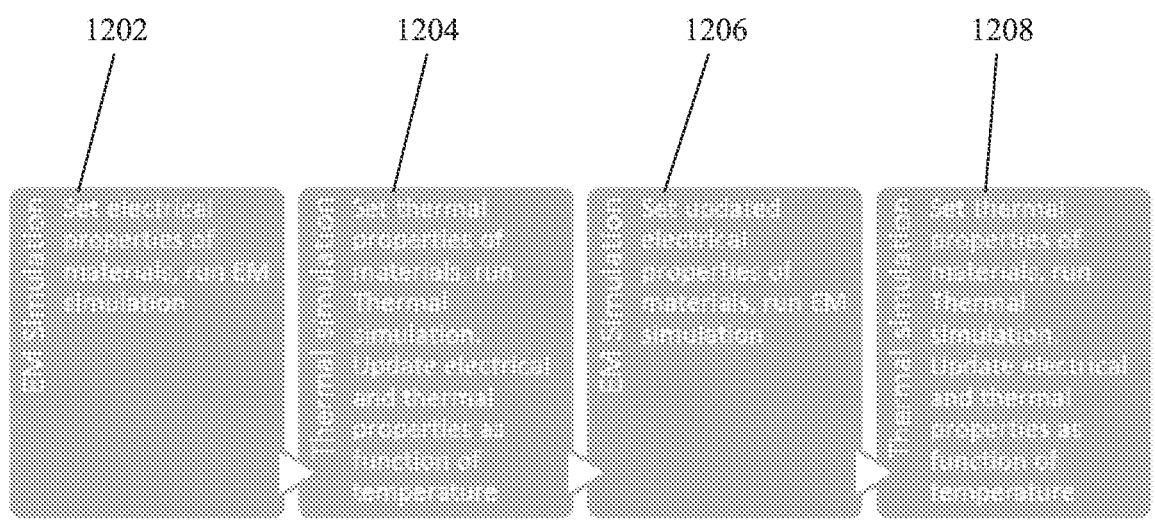
FIG. 12 is flowchart of a method for generating the thermal component of a generated simulation, in accordance with some embodiments of the present invention.

Reference is now made to FIG. 12, which is a flowchart of an exemplary method for generating the thermal component of the generated simulation, in accordance with some embodiments of the present invention.

In some embodiments, at 1202, the dataset of electric properties of the catheterization procedure materials are set based on the received values, for example, for a certain catheter, at a certain angle, pressure, and operating frequency (e.g., when performing an ablation procedure and/or as part of a measurement process). The electric properties of the catheterization procedure materials may include the dataset of a body portion of a patient including anatomical imaging data of the patient (optionally 3D data). The dataset may include the associated dielectric parameter values.

In some embodiments, the simulation is generated to simulate the electromagnetic fields on the catheter. In some embodiments, the power density loss (PLD) pattern is simulated.

In some embodiments, at 1204, the thermal properties of the tissues and/or catheterization procedure are set based on the received values. The PLD pattern may be used as a heat source for generating the thermal property component of the generated simulation. The thermal properties may be simulated over a period of time to obtain a temperature distribution pattern over the period of time, for example, based on the procedure. The period of time may represent a significant period of time, for example, based on cardiac output, based on the estimated time to navigate the catheter within the heart, and/or based on the time for performing an ablation.

The initial electrical and thermal property values are updated as a function of temperature based on the initial simulation.

In some embodiments, at 1206 and 1208, blocks 1202 and 1204 are iterated one or more times. During each iteration, the simulation may use the values calculated using the earlier simulation, to improve the accuracy and/or resolution of the updated simulated values. The blocks may be iterated until a stop condition is met, for example, a desired accuracy and/or simulation, and/or until the values remain unchanged within a tolerance requirement.

Referring now back to block 104 of FIG. 1, optionally, the generated simulation includes determination of a power loss density pattern. The PLD pattern may be generated for the tissue targeted for (or currently being) treated using RF energy. The PLD pattern may be estimated in time and/or space. Alternatively or additionally, the simulation includes determination of a temperature pattern. The temperature pattern may be generated for the tissue targeted or (or currently being) treated using RF energy. The PLD pattern may be estimated in time and/or space. The PDL pattern may be calculated for multiple points, for each set of electrode location (e.g., using the coordinates according to the externally applied electromagnetic field), the pressured applied to the tissue wall, and the angle of the electrode relative to the tissue. The PLD pattern may be used in the generated simulation to guide the ablation treatment.

The PLD pattern, and/or gasification transition pattern, and/or temperature pattern may be used to update the simulated electric fields for correction of coordinates determined using real-time measurements of the externally applied electric fields. The PLD pattern, and/or gasification transition pattern, and/or temperature pattern may affect the electric and/or thermal properties of tissues, which may alter the real-time measurements of the electric field and/or real-time measurements of the dielectric, electric, and/or thermal properties.

The PLD pattern, and/or gasification transition pattern, and/or temperature pattern calculated as part of the generated simulation may use the corrected catheter coordinates (and/or simulated catheter coordinates, and/or measured catheter coordinates) as input of the location of the catheter.

The PLD pattern may be calculated using equation (1):

$$PLD = \frac{1}{2}(\sigma + \omega \varepsilon_o \varepsilon'')|E|^2 = \frac{1}{2}\sigma_e |E|^2$$

where:
$|E|$ denotes the magnitude of E,
$\Omega = 2\omega f$, where f denotes the operating frequency in hertz (Hz),
$\sigma_e$ denotes an effective conductivity defined as $\sigma + \omega \varepsilon_o \varepsilon_g^N$.

The temperature pattern may be calculated based on an estimation of the rise of temperature, which may be estimated according to the continuity equation (i.e., equation (2)) that describes the simple case of electromagnetic heating where the temperature rises at a uniform rate:

$$\frac{\partial T}{\partial t} = PLD / \rho c_p$$

Where
$\rho$ denotes the density, and
$c_p$ denotes the specific heat.

Reference is now made to FIG. 13A, which is a graph depicting the calculated PLD pattern created by an electrode 1302 (e.g., RF ablation electrode(s)) in a tissue 1304, in accordance with some embodiments of the present invention. The PLD pattern may be calculated using equation (1). The PLD pattern may be used in the generated simulation described herein.

D denotes the ablation depth,
G denotes the gap (generally, D+G represents the wall thickness of the tissue),
V denotes the volume of ablated shape. Generally, the top view of an exemplary ablation region has an ellipse type shape. The ablation volume may be denotes by:
L denotes the length of the ablation region, and
W denotes the width of the ablation region.

Reference is now made to FIG. 13B, which is a graph depicting the calculated temperature pattern (in degrees Celsius) created by an electrode 1306 (e.g., RF ablation electrode(s)) in a tissue 1308, in accordance with some embodiments of the present invention. The temperature pattern may be calculated using equation (2). The temperature pattern may be used in the generated simulation described herein.

Optionally, the Gasification Transition (GS) of ablation using cryogenic energy at each possible ablation region is calculated. The GS may be calculated based on the location of each ablation region, the pressure, the angle of the catheter, and/or other values. Based on the generated simulation, the location, pressure, angle, and/or other values may be selected to achieve safe GS values, for example, according to a safety requirement.

Figure 3:
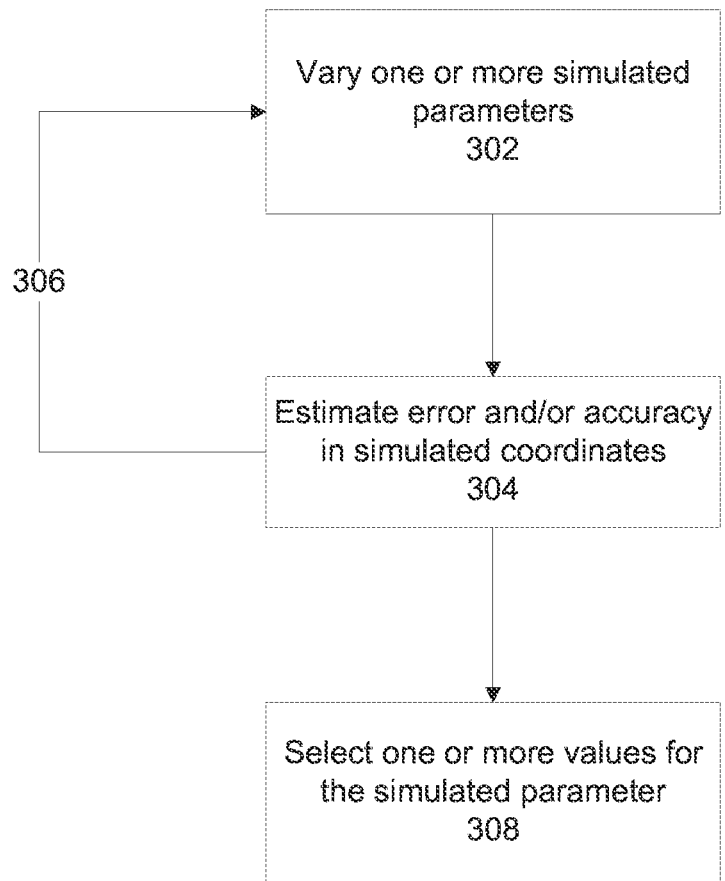
FIG. 3 is a flowchart of a method for selecting one or more parameters for tracking the position of an intra-body catheter, in accordance with some embodiments of the present invention.

Reference is now made to FIG. 3, which is a flowchart of a method for selecting one or more parameters for tracking the position of an intra-body catheter, in accordance with some embodiments of the present invention. The method may be used as part of a pre-planning phase, optionally executed off-line before the patient undergoes the procedure, for selection of parameters to use during the procedure. The method may select one or more of the electric and/or thermal parameters and/or the elements for generating the electric and/or thermal parameters based on the simulation. The parameters and/or elements may be selected to reduce the error in accuracy of calculating the coordinates of the distal end of the catheter, and/or to improve the accuracy thereof.

Alternatively or additionally, the method may select catheters for use in combination, such as selecting the combination of catheters to use, or selecting one catheter given another catheter is fixed. The catheters may be selected to reduce cross-talk, based on reducing the error in accuracy and/or improve the accuracy of calculating the coordinates of one or both catheters.

The method may select one or more of the following parameters: the placement position (e.g., location, angle) of one or more catheters, the administration and/or time and/or dose of drugs, the application of a mechanical force (e.g., to the tissue, as part of the treatment, or part of the navigation), the application of thermal intervention(s), and/or the timing and/or properties of signals transmitted into and/or out of the body.

For example, in terms of drug administration, free electrons serve as charge carriers, inside tissue ions (e.g., Na+, K+, Cl−) carry the electric current. Drugs that change blood volume and/or ionic channels, as well as dehydration, volume overload, hypernatremia, and hyponatremia affects the efficiency of RF ablation. Such effects may be simulated using the generated simulation and tested to select the optimal drug administration parameters (e.g., dose, timing of administration, type of drug). In another example, irrigation ablation catheters may load the patient with excessive fluids causing dilution and over-hydration. Such effects may be simulated over time and considered in the procedure (e.g., regions ablated 30 minutes after procedure start will behave differently than ablation of regions at the beginning of the procedure when fluids and/or other drugs are administered during the 30 minutes).

The method of FIG. 3 may be executed by system 200 of FIG. 2, for example, instructions to execute the method may be stored in program store 206 for implementation by processor 204.

At 302, the simulation may be executed (or re-executed) including a variation of one or more parameters.

Optionally, one or more parameters of one or more of the extra-body electrodes, are varied, for example, extra-body electrode location, size of transmitting electrode surface area, geometry of transmitting electrode surface area, electric field strength, electric current amplitude, and frequency of electric current.

Alternatively or additionally, the one or more parameters include one or more other simulated catheters (or of all simulated catheters), which may be based on off-the shelf existing EP catheters. Each catheter includes electrodes at a distal portion thereof that result in catheter cross-talk, which may reduce the accuracy of calculation of the coordinates of the distal end of each catheter.

Alternatively or additionally, one or more other parameters are set, for example, the placement of multiple catheters, the administration of drugs (including saline), the presence of disease, the effects of previous treatments, the application of mechanical force, the application of a thermal intervention, and the application of signal(s) transmitted to and/or from the inside of the body of the patient.

At 304, the code may estimate an inaccuracy in the simulation coordinates, and/or estimates the resolution of accuracy of the coordinates, based on the varied parameters. Alternatively or additionally, the code estimates the inaccuracy and/or the resolution of accuracy of the simulation coordinates for each simulated catheter in view of cross-talk between the catheters.

Optionally, the error and/or accuracy is estimated when the catheter(s) is in proximity to the target tissue (as that is where the highest accuracy may be desired).

At 306, blocks 304 and 302 are repeated, by varying the value of the parameter and re-executing the simulation (completed or partial) to estimate the accuracy and/or error in accuracy using the variation. Alternatively or additionally, the combination of catheters is varied.

Calibration may be iteratively performed to correct, for example, between the simulation dielectric and/or thermal space and the actual measured dielectric and/or thermal space. The calibration may correct for scaling and/or shifting differences, or other variations between the simulation and the real world. Optionally, a database of simulated values may be created and/or used to store previously calibrated simulation results. The previously calibrated simulation results may be re-used, for example, in another procedure of the same patient, to reduce the processing resources required to generate the simulation, by preventing or reducing the re-calibration.

At 308, the code may select the values of the varied parameter to reduce the inaccuracy and/or achieve the highest accuracy. Alternatively or additionally, the code selects the combination of catheters to reduce the accuracy error and/or achieve the highest accuracy in view of cross-talk. The code may select one or more of: the position placement of each of multiple catheters, the timing, concentration, and/or type of drug administered, the position and/or magnitude of the applied mechanical force, the position and/or temperature profile of the thermal intervention, and the strength, pattern, frequency, amplitude, and/or timing of signal(s) transmitted to and/or from the inside of the body of the patient.

Different results may be presented to the user (e.g. on display 232), to allow the user to select which treatment parameters and/or elements to use and/or catheters. For example, the code may select a size of the extra-body electrodes and/or catheter model that may not be in stock, in which case an alternative may be selected that is in stock to try and obtain similar accuracy. In other examples, the results presented to the user may include, for example, different positions for the multiple catheters, different drugs that may be administered and/or the timing of the dose, different possibilities for application of the applied force, different temperature profiles of thermal interventions, ablation parameters, and signal patterns for transmission into and/or out of the body.

The selection may be done in advance of the procedure, such as to allow obtaining the selected equipment. When the code selects the location for the extra-body electrodes, the skin of the patient may be manually marked (e.g., with a marker) in advance, for placement of the extra-body electrode during the procedure.

Referring now back to FIG. 1, at 106, the physical position of a physical catheter during the real catheterization procedure may be tracked, as the catheter is navigated inside the patient. Optionally, the physical tracking is based on impedance based mapping techniques, as described herein. It is noted that blocks 102 and 104 may occur offline, before the procedure has started.

Optionally, code stored in data repository 208 implementable by processor 204 of system 200 physically tracks coordinates of the position of the distal portion of the physical catheter within the physical body portion of the patient. The coordinates may be calculated according to physically applied electrical fields within the body portion and measurements of the electrical fields performed by electrodes 214 and/or sensors 228 at a distal portion of physical catheter 216 received via interface 212 and/or 226.

Alternatively, coordinates are provided to processor 204, calculated by navigation system 236 (e.g., impedance measurement based navigation system as described herein) via interface 234.

At 108, the code implementable by the processor(s) may register the physically tracked coordinates with the simulation coordinates. The registered coordinates may be analyzed to identify differences between the physically tracked location coordinates and the simulation coordinates.

The differences may include differences in absolute coordinate values. The differences may include differences in coordinate values considering an error in accuracy reading, for example, partial or lack of overlap in the coordinate values considering the margin of error in accuracy for the value. The difference may include differences in estimated precision of the coordinate values, for example, the physical coordinates accurate to within about +/−2 mm (millimeters) and the simulated coordinates accurate to within about +/−1 mm.

Optionally, the simulation location coordinates are calibrated according to a defined anatomical and physical location of the distal end portion of the physical catheter. For example, the user may manually mark on the screen displaying the simulated image of the dataset, the location corresponding to knowledge of the user (e.g., based on anatomical knowledge and catheter operation experience), for example, within the left atrial appendage. In another example, the code analyzes the movement of the catheter to detect physical locations within the simulated dataset image (e.g., displayed on the screen), for example, the catheter trapped within a cone shaped structure may indicate the apex of the left atrium. The calibrated simulation coordinates may be registered to the physical coordinates based on the registration. It is noted that the calibration of the simulation coordinates may occur iteratively to update the dataset, which may improve accuracy of the simulated coordinates, for example, as described with reference to block 114.

Alternatively or additionally, other calibration methods may be used, for example, when the physical catheter includes multiple electrodes with predefined known distances between the electrodes, the known distances may be used to calibrate the physical coordinates.

At 110, code implementable by the processor may correct the physically tracked location coordinates according to the registered simulation coordinates. For example, when the registered coordinates have overlapping ranges (considering the error in accuracy), with the simulation coordinates having lower error than the physical coordinates, the physical coordinate may be corrected to have the error range of the simulation coordinates. In another example, a weighing algorithm may calculate the corrected coordinates by assigning a calculated weight to the simulated coordinates, and correcting based on the weighted simulated coordinates.

At 112, code implementable by the processor may provide the corrected physically tracked location coordinates for presentation on display 232 via output interface 230. Alternatively or additionally the corrected coordinates may be forwarded to an external server, stored (locally or remotely), and/or undergo further processing (e.g., as described herein).

At 114, one or more of blocks 104, 106, 108, 110, 112, 116 (as discussed below) and 118 (as discussed below) are iterated.

Optionally, the iterations are performed until a stop condition is met, for example, identification of a template of signals that is indicative of achievement of a target, for example, indicative of achievement of a desired ablation pattern. The template may be created for each patient, a group of patients having one or more common characteristics, or a general template for all patients being treated. Exemplary stop conditions include the achievement of, for example, tissue coagulation, tissue edema, transmural ablation, continuous ablation line, and other indicators that are associated with effectiveness of the ablation procedure and/or safety of the ablation procedure. The template may be based on measured electrical and/or thermal properties described herein, and/or other sensed signals, for example, intravascular ultrasound imaging. Multiple templates may be available, for example, representing the desired ablation pattern. Template may be available representing partial achievement of the target ablation pattern, for example, about 25%, about 50%, or about 75% ablation achievement. The received signals may be correlated to identify the template with the highest correlation, and/or according to a correlation requirement representing similarity with the template. The template(s) may be created by applying one or more machine learning methods to experimentally collected and/or simulation generated data, for example, a statistical classifier may be trained to receives as input the sensed signals and generate an output of a category indicative of the achievement or lack of achievement of the desired ablation pattern. It is noted that the term template as used herein may mean a set of signature signals used by machine learning methods represented using the relevant data structure of the machine learning method.

Optionally, the iterations update the displayed location of the catheter within the displayed patient images on the screen, for example, as the catheter is navigated inside the body of the patient.

Optionally, the accuracy of the simulated coordinates is improved by the iterations, as described herein. Optionally, the iterations are performed to achieve a desired accuracy, for example, a target range and/or threshold. The target accuracy may be less than the accuracy of the measured physical coordinates. Optionally, the accuracy target is about +/−1 millimeter for the corrected physically tracked coordinates.

It is noted, that the physically tracked coordinates (non-corrected) may have an accuracy of about +/−3-5 mm, or about +/−2 mm. Improving the corrected coordinates to an accuracy of about +/−2-3 mm, or about +/−1 mm may allow, for example, for improved precision in targeting GPs. Accuracy may be defined, for example, as an average error over the mapping volume (e.g., the full volume, or the sub-volume). In another example, accuracy may be defined as the true error between the anatomical landmarks, and/or the true error between ablations at different cardiac regions.

Figure 4:
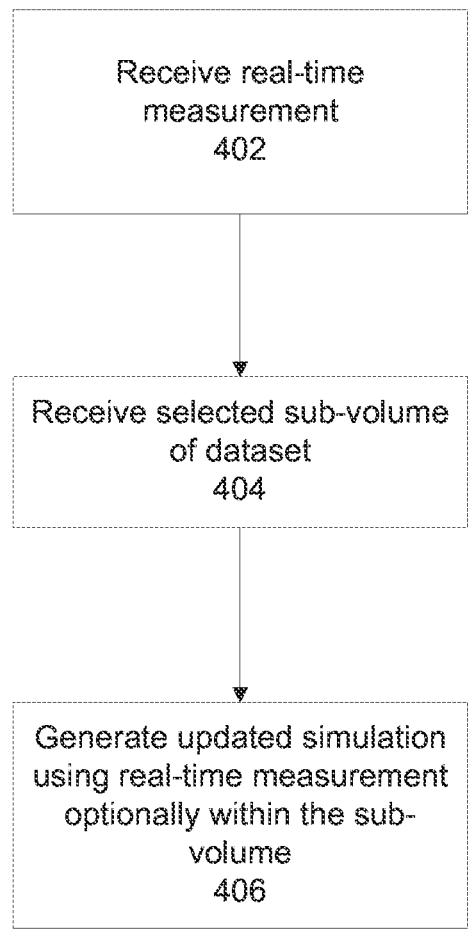
FIG. 4 is a flowchart of a method of iteratively updating a simulation of the position of an intra-body catheter, in accordance with some embodiments of the present invention.

Reference is now made to FIG. 4, which is a flowchart of a method of iteratively updating a simulation of the position of an intra-body catheter, in accordance with some embodiments of the present invention. The method of FIG. 4 may be executed in real-time, during the procedure, based on real-time measurements acquired from the body of the patient during the procedure. The method of FIG. 4 may be executed by processor 204 implementing code stored in program store 206. The time interval for updating the simulated electrical and/or thermal properties is, for example, every about 1 second, or every about 5 seconds, or every about 10 seconds, or within the range 3-10 seconds. The resolution time interval may be preset (e.g., constant), or dynamically selected, for example, updated at a lower frequency when the catheter is far from the target, and updated at a higher frequency when the catheter is closer to the target.

It is noted that for computationally intensive and/or complicated simulations, the simulation does not necessarily need to be entirely re-calculated during every iteration. An initial base data set used by the simulation may be generated and stored, for example, in a database (e.g., based on electromagnetic and/or tissue parameter analysis of possible ablation points in a defined ablation space). For each point, for each predefined internal of time (e.g., every about 1-10 seconds), electric and/or thermal parameter values may be calculated (e.g., voltage, current, impedance, optionally in vector format) and used to update the generated base dataset. In real-time, correlations may be found between the measured electrical and/or thermal parameter values and the base dataset values. The correlation may be used to update the generated simulation in real-time, which may improve performance of the computing unit updating the generated simulation, for example, by reducing the time and/or processing resources used to updated the generated simulation.

At 402, the code may receive a real-time measurement of one or more dielectric and/or thermal parameter(s) of one or more intra-body tissues, for example, via sensor interface 226 and/or electrode interface 212.

The dielectric parameter(s) may be impedance and/or conductivity. Optionally, the dielectric parameters correspond to the dielectric parameters associated with the imaging data of the dataset.

Optionally, one or more additionally measured electrical properties are received and used to update the simulated dielectric parameters, for example, current, and voltage. It is noted that commonly available catheters and/or commonly available sensors may be used, for example, voltage may be measured, from which the other dielectric parameters may be calculated or estimated.

Optionally, the impedance of the myocardium (and/or other tissues) includes the real and/or imaginary components. Optionally, the impedance is acquired in at least two frequencies. Impedance measurements may be performed substantially concomitantly, such as simultaneously or sequentially for each frequency with relatively short and/or insignificant delays between the measurements.

Optionally, the impedance of the myocardium (and/or other tissues) is measured at a frequency selected as being away from existing commercial intra-cardiac ECG recording system filters, to prevent and/or avoid interference with the ECG recordings (to the ECG and/or to the impedance measurement), for example, about 20-100 kilohertz (KHz), or about 40 kHz. Alternatively or additionally, the impedance of the myocardium (and/or other tissue) is measured at a frequency selected as being away from existing RF generating system (e.g., ablation system) and/or from folding frequencies thereof, optionally at least 500 kHz away, to prevent and/or avoid interference with the RF ablation system (to the RF ablation and/or to the impedance measurement), for example, 1 megahertz (MHz), which may be selected for measuring frequency and/or accurately separating between healthy tissues and/or between healthy and malignant samples, and/or for helping to distinguish between fibrotic tissue and viable myocardium.

Optionally, individual calibration per catheter (as described herein) and/or simulation of the catheters (as described herein) is performed, before and/or during measurement of the myocardial impedance. The simulation and/or calibration may improve accuracy of the measurement, by accounting for and/or correcting parasitic capacitance and/or cross talk that occur along long catheters and/or connection cables, as described herein.

The intra-body tissue may be blood. The blood dielectric and/or thermal parameter may be measured, for example, by an indwelling catheter, and/or by retrieving blood samples for analysis in an external machine. Blood flowing past the treatment elements of the catheter may be heated when the catheter is applying energy, for example, during an ablation procedure. As such, correcting the coordinates to account for changes in blood flow dielectric and/or thermal parameters due to the heating effect may improve the accuracy of the coordinates.

The intra-body tissue may include the target tissue and/or nearby tissue, such as the tissue targeted for ablation, for example, myocardium (e.g., when the heart is being treated), tumor tissue, neural tissue (e.g., when epicardial ganglionated plexi are being ablated and/or blocked) or other tissues being treated. The dielectric and/or thermal properties of the myocardium may be measured, for example, by the catheter described with reference to FIGS. 8A-8C. The target tissue and/or nearby tissue may be heated when the catheter is applying energy, for example, during the ablation procedure. As such, correcting the coordinates to account for changes in tissue dielectric and/or thermal parameters due to the heating effect may improve the accuracy of the coordinates.

Other electrical properties of tissues (e.g., blood, bone, lungs, heart) that may be measured include relatively permittivity and/or conductivity. Optionally, the electrical properties are measured at the operating frequency (or frequencies). The measurement at one or more frequency may be used to estimate losses occurring at each frequency. Other exemplary electrical properties that may be measured to estimate the reaction and/or changes to the applied electric fields used to navigate the catheter includes voltage, and current (complex and/or absolute values).

Alternatively or additionally, additional data is gathered in real-time, and used to update the generated simulation. For each data item, deviations from the simulated data item may be calculated and used to update the simulation, e.g., to better reflect actual procedure conditions. The additional data may affect the electric and/or thermal property values of the tissues, for example, in simulating the location of the catheter, simulating the effect of application of force by the catheter to the tissue, and/or simulating the ablation treatment. Updating and/or correction of the additional data may improve the simulation based on the electric and/or thermal property values of the tissues. The additional data may be manually entered by the operator (e.g., patient weight), obtained from an interface to one or more external devices that perform measurements (e.g. blood pressure machine), obtained from sensors (e.g., catheter temperature), and/or obtained by accessing an external data source, such as a database (e.g., patient medications from an electronic medical record).

Exemplary additional data gathered in real time include one or more of:

Catheter potential—may be used to update the simulated catheter potential.

Body surface potential—may be used to update the simulated body surface potential (e.g., for correcting the electric fields used to guide the catheter).

Catheter temperature—may be used to update the simulated catheter temperature, when the catheter is delivering ablation treatment, and/or when the catheter stopped the treatment.

Patient weight and/or blood pressure—may be used to improve the simulation of the deformation of the tissue as a reaction to force applied by the catheter's distal end on the tissue, such as during ablation treatment. The patient's weight and/or blood pressure may reflect pre-existing internal mechanical forces being applied to the tissue. The deformation affects the electric field values and the resulting simulated temperature pattern of ablation.

Pressure applied by the distal end of the catheter to the tissue—may be used to improve the simulation of the deformation of the tissue.

Catheter irrigation rate—may be used to improve the estimation of the boundary conditions around the simulated distal end region of the catheter. The catheter irrigation rate affects the electric field values and the resulting simulated temperature pattern of ablation.

Drug administration—may be used to improve the estimation of the electric parameter values of the tissues, due to ionic effects of the drugs and/or saline. The electric properties of cells are affects by certain drugs and/or fluids.

ECG—may be used to improve the estimation of the electric parameter values of the tissues. The electrical activity of the heart may dynamically alter the electric parameter values of the tissues, which may be incorporated into the simulation.

Energy application data—may be used to estimate the amount of applied power that is absorbed (e.g., by flowing blood), such as over a period of time. The absorption of energy affects the energy required to perform the desired ablation treatment.

Optionally, real-time measurements of the electric fields generated by the externally located body patches (also referred to herein as extra-body electrodes) are performed in response to an injected signal. Optionally, the injected signal, for example, a voltage pattern, a current pattern, or other signal pattern, is applied to the body electrode patches located externally to the body of the patient (i.e., the patches used to create the electric fields which are used to help navigate the electrode). The injected signal may be superimposed on the electric fields. The injected signal may be sensed by the sensors on the distal portion of the electrode used to sense the applied electric field. An analysis may be performed, to compare the sensed injected signal to the applied injected signal. The analysis may determine the correction to be applied to the coordinates determined used the electric fields. The correction based on the injected signal may improve the accuracy of the generated simulation.

The signal may be injected before the ablation, during the ablation, and/or after the ablation. The ablation process may change the electric and/or thermal property values of the tissues in proximity to the sensors on the distal end of the catheter. As such, without correction, the sensors may sense a change in location of the catheter using the externally applied electric fields due to the change in the tissue electric and/or thermal property values, even when the catheter remains substantially in the same position. The analysis of the injected signal may correct the measurements of the externally applied electric fields, to correct the coordinates as the ablation proceeds, and avoid or prevent errors due to the change in tissue electric and/or thermal property values due to the ablation.

Optionally, at 404, the code may receive a selected sub-volume for the iteration. The sub-volume may be selected from the dataset, automatically and/or manually. The sub-volume defines the region for the update of the simulation in the iteration. Updating the sub-volume instead of the entire (or larger) dataset may allow for faster iterations and/or using fewer computing resources. For example, generating the entire simulation may require 30 minutes using a certain processor, which each iteration may be performed in 30 seconds using the same processor for a relatively small sub-volume.

Sub-volumes may be manually selected, for example, by the user drawing a box (or other shape) on the display, defining the sub-volume within the displayed anatomical image.

Alternatively or additionally, the sub-volume may be automatically selected by the code, optionally based on a volume (e.g., box) that includes the target tissue in near proximity to the distal end of the physical catheter.

Optionally, the iterations are performed with decreasing volumes of the sub-volume, optionally automatically, as the distance between the distal end of the physical catheter and the target tissue decreases (e.g., as the operator navigates to the catheter to the target tissue). In this manner, the accuracy of the position of the catheter may automatically increase with the iterations as the catheter is being navigated towards the target tissue. Increasing accuracy may be needed to guide the catheter to the target. For example, during introduction of the catheter (e.g., within the femoral artery) an accuracy of about +/−5 mm may be obtained (which may be sufficient within the femoral artery), during navigation inside the heart chambers an accuracy of about +/−3 mm may be obtained, and during fine navigation to position the ablation electrodes for ablation, an accuracy of about +/−1 mm may be obtained.

Optionally, the iterations are performed according to the procedure being performed. Optionally, the sub-volumes are selected according to changes in the location of the catheter, for example, as the catheter is performing an ablation in one spot and moves to a neighboring spot, the new sub-volume is selected according to the neighboring spot that the catheter is treating. Optionally, the new sub-volume may include regions of the previous sub-volume, such as one or more overlapping regions, or may include the entire previous sub-volume. Inclusion of the previously treated region within the previous sub-volume may be used to improve simulation of the state of the target tissue within the new sub-volume, for example, by accounting for physical changes of the previously treated tissue that affect the thermal and/or electrical properties of the tissues at the new treatment location.

Optionally, the iterations are automatically performed, for example, during the procedure, for example, according to a predefined period of time, such as every 1-10 seconds.

At 406, the code may generate an updated version of the simulation by updating the initial estimated value (or the previous measured value) of the dielectric and/or thermal parameter value with the real-time measurement. The updated simulation is used to adjust the corrected coordinates, and/or re-calculated the corrected coordinates.

Optionally, the updated simulation is performed for the entire region and not a sub-volume, e.g., block 404 may be omitted.

The simulation may be updated according to real-time data associated with a real-time state of the patient during the procedure, for example, one or more of:

Catheter location—the actual location of the distal end region of the catheter contacting tissue and/or the angle of the contacting distal end region relative to the tissue improves the quality of the simulation of the ablation region.

Body electrode patch location—the actual location of each body patch (which is used to create electric fields used for navigation of the catheter) may be used to improve the simulation of the electric fields, which may improve accuracy of the location of the catheter using the electric fields. Since different body tissues have different impedance values and/or differ in electric and/or thermal property values, the actual location of the patches affects the measurements of the electric fields performed by sensors on the catheter. The actual location of the patch may improve the simulation by reducing the error between the simulated location of the catheter and the actual location of the catheter.

Catheter temperature—may be used to update the simulated boundary conditions in the thermal parameter component of the simulation.

Catheter sensed pressure—may be used to update the simulated application of force to the tissue by the distal end portion of the catheter.

Catheter sensed data—may be used to update the simulated ablation, for example, by updating the simulation according to the actual operating frequency, which may be different than the simulated operating frequency.

Body patches sensed information (the body patch electrodes may be used to sense the catheter inside the body)—may be used to update the simulated location of the catheter and/or to reduce the error relative to the actual location of the catheter.

Ablation energy deposits—may be used to update the simulation with the actual applied energy and the actual dissipated energy (i.e., not used to ablate, due to losses into nearby tissue).

Optionally, the generated simulation may be used to guide therapy of the interventional procedure, for example, ablation using RF energy at one or more regions using the catheter. Optionally, the generated simulation includes an estimated PDL of the ablation RF energy at the one or more points. The estimated PDL may be determined based on real-time values (e.g., which may be provided in block 402), optionally one or more of: location of the ablation electrode(s) of the catheter (e.g., based on the coordinates according to the applied electric fields), the pressure the catheter applies to the tissue and/or the angle of the ablation electrode.

Referring now back to FIG. 1, optionally, at 116, the extent of the ablated target tissue, such as the size (e.g., dimension about parallel to a tissue depth axis), volume, and/or depth (e.g., along the depth axis) may be estimated by the code implementable by the processor. Alternatively or additionally, the quality of the contact force between the distal end of the catheter and the tissue in contact with the catheter is estimated by the code implantable by the processor.

Inventors discovered that the measured impedance between an electrode (or sensor) on the catheter (e.g., distal end thereof) and one or more other electrodes (e.g., on the same catheter, on another catheter, and/or an extra-body electrode) is correlated with desired contact between the catheter and tissue (e.g., target tissue and/or nearby tissue). Inventors discovered that although there is a large variance in the relation between the applied force and the impedances, the variance of the contact estimation may be significantly reduced by taking multiple reading samples from different locations of the same tissue, the same organ, and/or from other similar organs (e.g., of living subjects, of living mammals, of human cadavers, of slaughtered animals).

Figure 10:
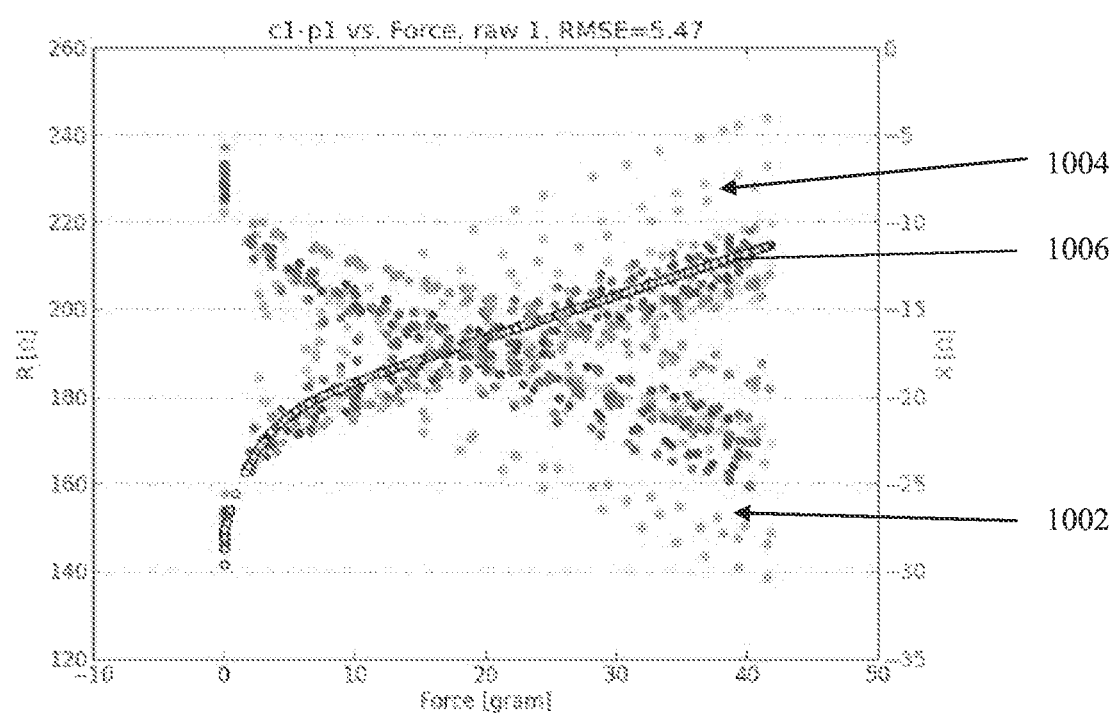
FIG. 10 is a graph of an example of multiple impedance measurements obtained by an electrode on a catheter, and an associated measured force, useful for generating a model for real-time force estimation based on real-time impedance measurements, in accordance with some embodiments of the present invention.

Inventors discovered that a set of such measurements, for example, as depicted in FIG. 10, may serve as a basis to generate a model for estimating contact force according to real-time impedance measurements in the patient, for example, by generating a trained statistical classifier, one or more correlation functions, and/or other learning methods. The real-time impedance measurements may be complex value, magnitude or imaginary part of the impedance.

Reference is now made to FIG. 10, which is a an example of a graph plotting multiple impedance measurements obtained by an electrode on a catheter, and an associated measured force, useful for generating a model for real-time force estimation based on real-time impedance measurements, in accordance with some embodiments of the present invention. A single point on the chart represents a measurement at a specific location under a given force. Dots 1004 represent the real part of the impedance. Dots 1002 represent the imaginary part. The set of measurements were obtained at different locations of the same organ. The average relation is described by dots 1006, obtained by fitting a model to the set of points. Note the relatively large variance around the average.

A conjecture reached by the inventors for the variability of the impedance (given a fixed level of force) is that the impedance is directly related to variability in the quality of the contact between the tip of the catheter and the tissue. Inventors hypothesize that the contact is determined not only by the force applied to the tip, but also by micro-structured contact which is formed between the catheter tip and the tissue.

Optionally, the estimated applied contact force is selected from the group: suboptimal contact force, optimal contact force, and excessive contact force.

Figure 11B:
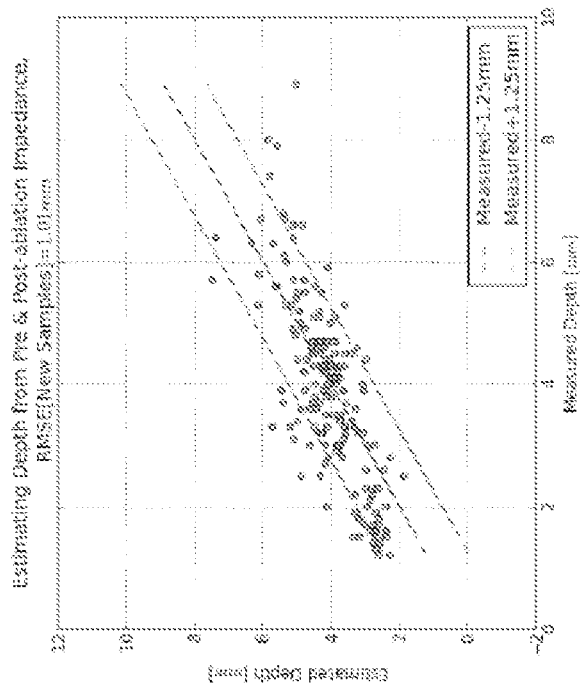
FIGS. 11A-11B are example graphs depicting a correlation between an estimation of the depth of an ablated tissue lesion based on impedance measurements, and a measured depth, in accordance with some embodiments of the present invention.

Alternatively or additionally, another trained machine learning method is applied to correlate the one or more impedance measurements with an estimated dimension of the ablated tissue lesion, optionally one or more of: depth, surface diameter, and volume. Optionally, the real-time impedance measurements are obtained before the ablation procedure. Alternatively or additionally, the real-time impedance measurements are obtained after the ablation procedure. For example, as shown in FIGS. 11A-11B, which are example graphs depicting the correlation between an estimate of the depth of an ablated tissue lesion based on impedance measurements, and a measured depth, in accordance with some embodiments of the present invention.

Figure 11A:
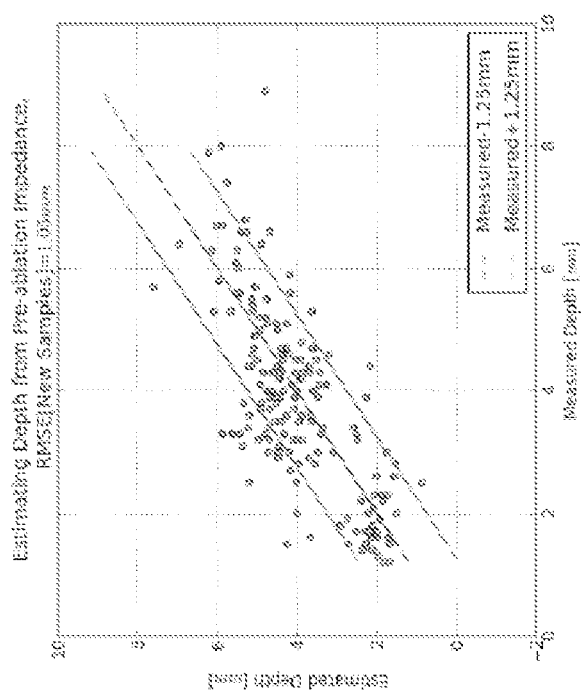

FIG. 11A depicts an estimated depth of the lesion based on pre-ablation impedance values measured between an electrode of the ablation catheter and one or more other electrodes (e.g., body patch electrodes). FIG. 11B depicts an estimated depth based on pre and post-ablation impedance measurements.

Referring now back to FIG. 1, alternatively or additionally, one or more other parameters are estimated based on the dielectric and/or thermal measurements (e.g., impedance), for example, temperature of the target tissue and/or nearby tissue, and/or spatial pattern of ablation. The parameters may be estimated, for example, by machine learning methods that receive the dielectric and/or thermal measurements (and/or other values), apply a machine learning algorithm (e.g., statistical classifier), and output an estimated value. The estimations may be performed in real-time based on real-time measurements. The estimated values may be outputted to the user, which may aid the operator in deciding on the treatment, for example, whether the desired temperature is reached and/or whether the desired ablation pattern is being obtained.

The machine learning methods described herein may be applied to the measured impedance value by code stored in the program store, implementable by the processor of the computing unit. The machine learning method (e.g., trained statistical classifier, one or more functions, a look-up table, a parametric model, support vector machine with optional radial basis function, or others) may be implemented by the code, which may be downloaded, for example, from a central server, and/or locally stored.

The methods described herein may allow for faster estimation (e.g., close to real-time) of the extent of ablation, for example, as compared to methods that require additional time to allow edema to resolve.

Figure 5:
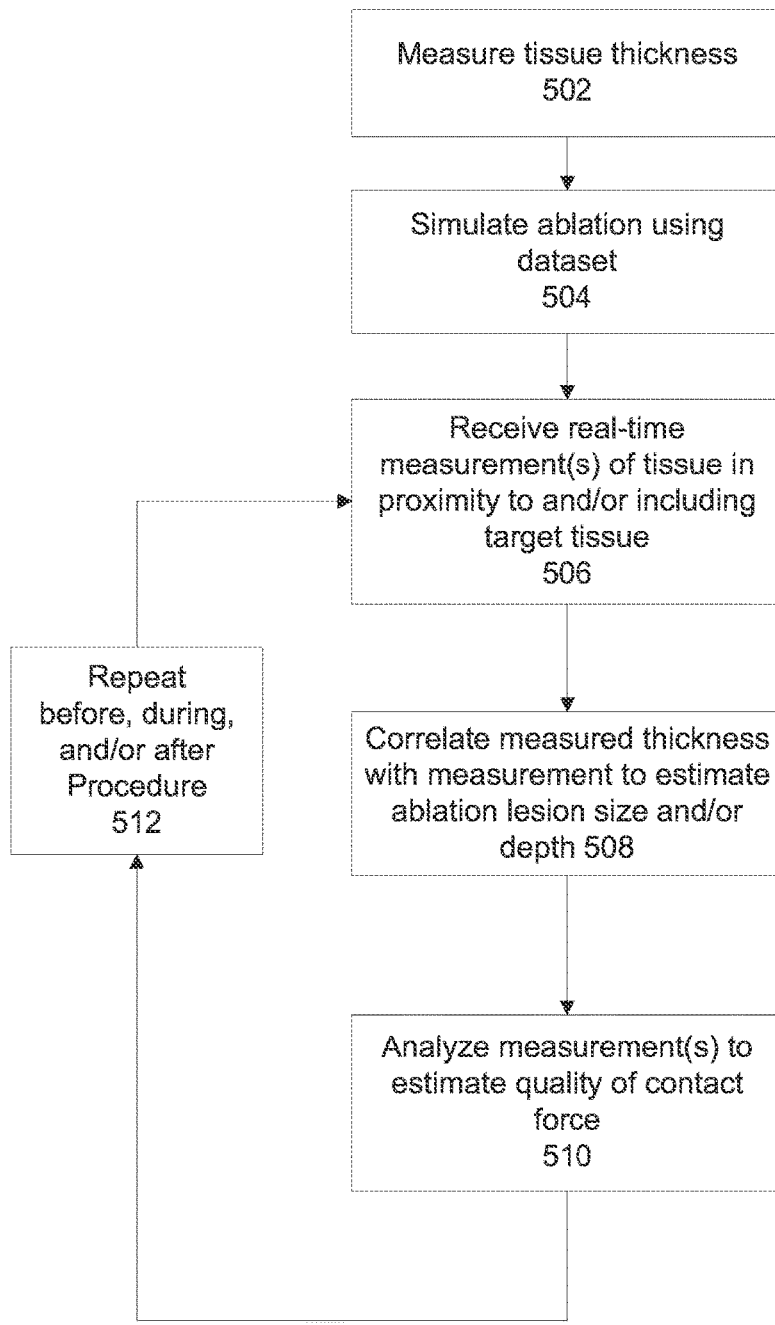
FIG. 5 is a flowchart of a method for estimation volume and/or depth of an ablated lesion, and/or for estimating a contact force applied by the intra-body catheter to a tissue, in accordance with some embodiments of the present invention.

Reference is now made to FIG. 5, which is a flowchart of a method for estimating volume and/or depth of an ablated lesion, and/or for estimating a contact force applied by the intra-body catheter to the contacting tissue, in accordance with some embodiments of the present invention. The method may estimate the contact force according to one or more measurements performed of the contacting tissue, optionally the impedance and/or conductance. Optionally, the method estimates the quality of contact force according to a categorization into one of multiple categories, which may be clinically relevant, instead of, for example, calculating an absolute force measurement.

Optionally, at 502, a thickness of the tissue in contact with the distal end of the catheter, which may include a target tissue for ablation, may be measured or calculated. The measurement may be performed manually by the user via the screen and/or user interface or automatically by the code according to the dataset and position of the distal end of the catheter. The thickness may be calculated from one or more anatomical images of the patient (e.g., left atrial wall thickness—LAWT, may be calculated from a patient's CT image).

The thickness of the tissue may represent the extent of the allowed or desired ablation. For example, in some cases, transmural ablation across the entire depth may be desired, such as to ablate the entire tissue depth. In other cases, the ablation is to be performed without reaching the entire depth, such as to prevent perforation.

At 504, the simulation may be executed (or has been executed in block 104) to include a simulated ablation of the target tissue, for example, calculated using a model, based on experimental data, and/or based on thermodynamic equations. The simulation may be of ablation by the simulated catheter according to the real-time location of the physical catheter, and/or the simulation may be performed in advance, of the simulation location of the simulated catheter.

The simulation of ablation of the target tissue may be part of the pre-planning phase and may be used to select one or more catheters for ablation, ablation parameters (for example: ablation frequency and/or power etc.). The simulation may also provide the user (e.g., physician) with a forecast success criteria of the simulation to enable the user to select the one or more catheters for ablation, ablation parameters the like. The process may be iterated until optimal results are obtained.

Optionally, the simulation is an EP ablation, for example, a radiofrequency (RF) ablation procedure.

The simulation may be performed according to a simulated optimal contact force between the distal end portion of the simulated catheter and tissue in proximity to the target tissue. The simulation may be performed according to the current estimated contact force (e.g., as estimated herein).

Optionally, the simulation of the ablation is according to one or more ablation parameters (e.g., voltage, current, frequency, and/or ablation electrode surface area dimensions). The ablation parameters may be varied (e.g., as described herein) for selection of optimal values, may be automatically determined, and/or may be selected by the user.

At 506, the code may receive one or more measurements of a dielectric and/or thermal parameter of tissue in proximity to the target tissue and/or including target tissue. The measurement may be of the myocardium (as described herein), and/or of the tissue in contact with the catheter ablation electrodes (e.g., by one or more electrodes and/or sensors on the physical catheter) and/or other tissue (e.g., blood, as described herein).

Optionally, the measurement(s) is performed iteratively, before an ablation of the target tissue, during the ablation, and/or after the ablation of the target tissue.

Optionally, the measurements are performed in at least two frequencies, by the same sensor and/or electrode or different sensors and/or electrodes. The different frequencies may improve accuracy of the reading. The two frequencies may be selected to provide independent measurements, without significant interference, and/or interference that may be accounted for and removed.

Optionally, at 508, the code may correlate the measured thickness with the received dielectric and/or thermal parameter to estimate the lesion volume and/or lesion depth. The correlation may correct the estimated lesion volume and/or lesion depth. The correlation may be used to simulation the lesion volume and/or lesion depth.

Optionally, at 510, the code may correlate the measured dielectric and/or thermal parameter(s) to estimate a quality of the contact force relative to the simulated optimal contact force. The correlation may be performed, for example, by a statistical classifier that receives the parameter values and maps the values to one of multiple force quality categories, by a function, or other methods. The classifier may be pre-trained, for example, using experimental data and/or simulated data.

Optionally, the estimated quality of the contact force is categorized into one of the categories: suboptimal contact force, optimal contact force, and excessive contact force. The categories may be more clinically relevant to the operator, for example, relative to absolute force measurements. The categories may simply represent to operator if the applied force is right, more force is needed, or the force is to be reduced.

At 512, one or more blocks 506, 508, and 510 are iterated, for example, before the ablation, during the ablation, and/or after the ablation.

Figure 6:
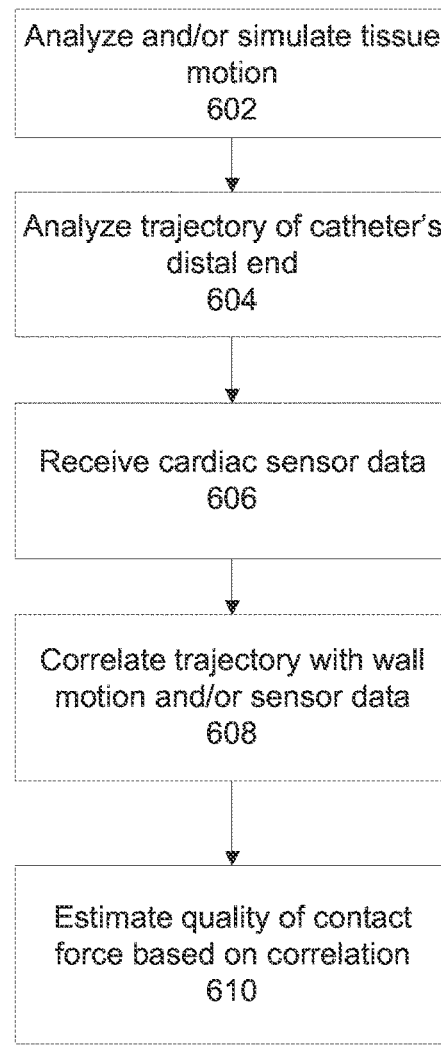
FIG. 6 is a flowchart of another method for estimating quality of contact between the intra-body catheter and a tissue based on tracking a trajectory of motion of the contacting catheter portion, in accordance with some embodiments of the present invention.

Reference is now made to FIG. 6, which is a flowchart of another method for estimating quality of contact between the intra-body catheter and a tissue based on tracking a trajectory of motion of the contacting catheter portion, in accordance with some embodiments of the present invention.

At 602, the code may receive and/or analyze measurements of and/or simulates motion of pulsating tissue in contact with or in near proximity to the distal end of the catheter (e.g., the ablation electrodes) over a time range. The time range may include at least one cardiac cycle, optionally several cycles.

The measurements may be performed, for example, from image data. The simulation may be performed based on the simulation dataset.

The tissue pulsates due to the beating motion of the heart.

At 604, the code may analyze the coordinates of the position of the distal portion of the physical catheter over a time range (optionally the same range as in block 602), to identify a motion trajectory.

The time range may include one or more cardiac cycles.

Optionally, at 606, the motion trajectory of the distal end of the catheter and/or the motion of the pulsating tissue may be correlated by the code to cardiac contractility data, for example, gated to a real-time ECG measurement (which may be obtained using external devices and/or standard methods).

At 608, the code may correlate the trajectory of the distal portion of the catheter with the motion of the pulsating tissue. The correlation may be performed according to the cardiac contractility data.

At 610, the code may estimate a quality of contact between the distal portion of the physical catheter and the pulsating tissue portion according to an analysis of the correlation. Optionally, the analysis is performed according to the cardiac contractility data. The code may classify the quality of contact, for example, according to a statistical classifier, a function, or a model.

For example, high correlation of movement between the catheter's distal end and the pulsating tissue that matches with the cardiac contractility data may be classified as good quality contact. For example, poor correlation of movement between the distal end and the pulsating tissue may be classified as insufficient contact force (e.g., the distal end doesn't always touch the pulsating tissue). For example, high correlation between the movement of the distal end and the tissue, but poor correlation with the cardiac contractility data may be classified as excessive force (e.g., too much force limits motion of the tissue).

Referring now back to FIG. 1, optionally, at 118, the code implementable by the processors may identify regions of fibrotic tissue within the patient. The identified fibrotic regions may be mapped to the displayed anatomical images of the patient, for example, marked by a distinguishable color from non-fibrotic tissue.

In one example, the fibrotic regions may be avoided when positioning the catheter for ablation (e.g., by manual observation and/or by code automatically generating a warning). In another example, non-fibrotic regions between or in proximity to the fibrotic regions are identified (manually by the operator or automatically by code) for additional ablation, such as when the previous ablation has been incomplete.

Figure 7:
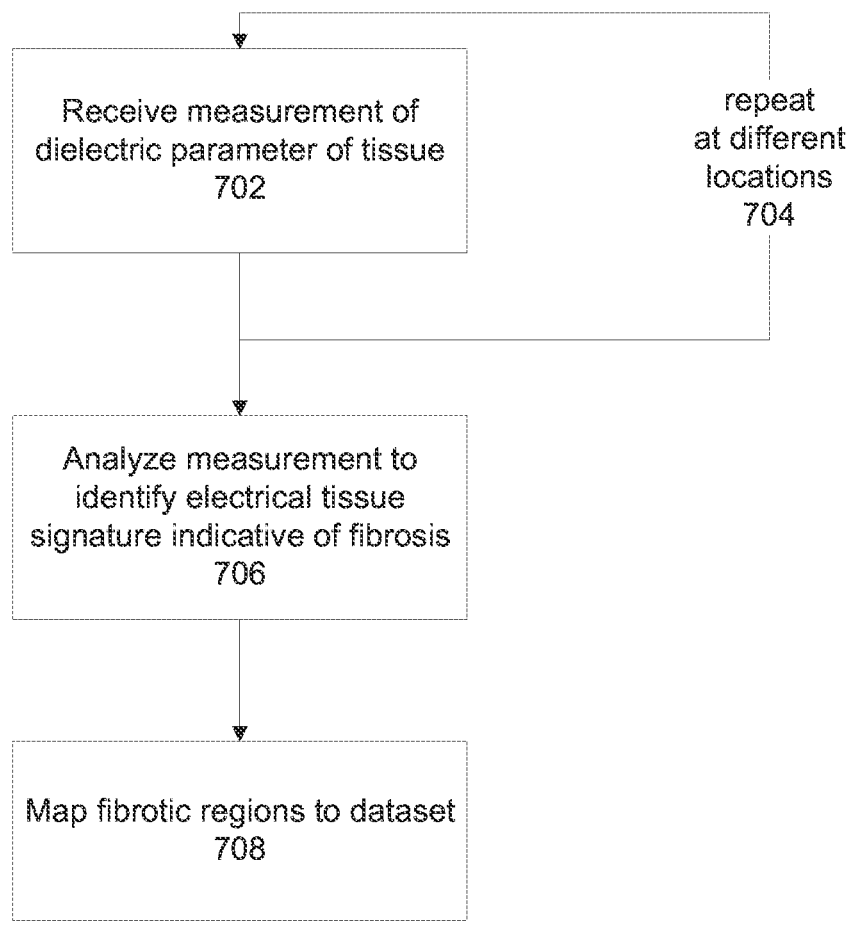
FIG. 7 is a flowchart of a method for identifying regions of fibrotic tissue, in accordance with some embodiments of the present invention.

Reference is now made to FIG. 7, which is a flowchart of a method for identifying regions of fibrotic tissue, in accordance with some embodiments of the present invention.

At 702, the code may receive one or more measurements of dielectric and/or thermal parameter(s) of the tissue in proximity to or of the target tissue, for example, impedance (e.g., complex impedance) and/or conductance.

Each measurement may be associated with the position of the distal end of the catheter when the measurement is obtained.

The measurements may be obtained from one or more electrodes and/or sensors of the physical catheter, for example, at the distal end of the catheter.

At 704, multiple measurements may be performed at multiple locations in proximity to the target tissue. For example, the measuring catheter is displaced (e.g., manually by the operator or automatically by a robot) along the surface of the tissue, to cover a desired area.

At 706, the code may analyze the measurement associated with one or more of the locations to identify an electric and/or thermal tissue signature indicative of one or more fibrotic tissue regions. For example, a band of fibrotic tissue (e.g., due to a scar), a circular clump of fibrotic tissue (e.g., due to a previous ablation), and/or an irregular shape (e.g., due to naturally occurring fibrosis). The analysis may be based on the imaginary value of the measured impedance (e.g., when the electric tissue signature includes impedance measurements).

At 708 the code may map the identified fibrotic tissue regions to the dataset. The dataset may be provided for visual presentation that may distinguish the fibrotic regions, for example, by a different color. The dataset including the fibrotic tissue regions may be provided as input to the simulation, e.g., when ablation of the target tissue is simulated.

Reference is now made to FIG. 8A, which is a schematic of a catheter for measuring one or more dielectric and/or thermal properties of tissues located within a narrow body region, for example a collapsed potential tissue space, for example, lung tissue within the pleural space, or the myocardium from within the pericardial space (depicted as exemplary, but is to be understood as applying to other similar body regions such as the pleural space), in accordance with some embodiments of the present invention. Catheter 800 is designed to physically isolate the parietal pericardium from the visceral pericardium region in proximity to the sensors measuring the dielectric and/or thermal properties. Catheter 800 may measure the impedance and/or conductance of the myocardium. The measurements may be more accurate and/or more precise over other methods, due to the isolation of the parietal pericardium, which may reduce errors (e.g., due to interference) due to effects of other nearby tissues in contact with the parietal pericardium.

Catheter 800 may be used to collect real-time measurements of the dielectric and/or thermal properties of the myocardium during the procedure, for improving the accuracy of the location of the catheter and/or other features, as described herein. Catheter 800 may be integrated with system 200. Optionally, sensors 810 are in communication with sensor interface 226 of unit 202. Unit 202 may include code to receive signals from the sensors and calculate the impedance and/or conductance of the myocardium. Alternatively or additionally, catheter 800 is a separate system, with measurements of the myocardium being manually entered into system 200 via user interface 224.

Optionally, sensors 810 are designed to measure the impedance at two or more frequencies, simultaneously and/or sequentially. For example, the signal may be applied as an input into a first sensor 810 (e.g., proximal sensor) and measured at a second (or additional) sensor 810 (e.g., distal sensor). Sensors 810 may be designed to measure a first frequency in the range of about 20-100 kHz (e.g., about 40 kHz) and a second frequency of about 1 MHz. There may be, for example, two sensors, or four sensors, or other numbers of sensors. Sensors 810 may be designed to include the real and/or imaginary components of the impedance measurement.

Catheter 800 is illustrated within a pericardial space 802, which is located between a parietal pericardium 804 (which is in contact with other organs and/or tissues, such as large blood vessels and the lungs), and a visceral pericardium 806 which overlies and is attached to a myocardium 808 of a heart of the patient. For completeness, an endocardium 814 is the inner layer of the heart wall, which may form the inner surface of the heart chamber.

Catheter 800 may be inserted into pericardial space 802, for example, over a guidewire and/or sheath, which may be deployed via a needle having lumen via a sub-xiphoid approach or other approaches.

Optionally, the distal end portion of catheter 800 is designed for expansion within the pericardial space, for example, self-expansion (e.g, made from Nickel-Titanium or other memory metals), and/or balloon expandable. Catheter 800 may be expanded from a first contracted stated in which the distal end portion is sized for delivery into the pericardial space, to a second expanded state, in which the sensors contact the visceral pericardium and the isolation element physically isolates the region between the sensors from the parietal pericardium. The expansion may be based on shape and/or geometrical changes of the isolation element.

Catheter 800 may include spaced apart sensors 810 (e.g., microelectrodes) disposed at a distal end portion thereof, for example, two sensors spaced apart along the length of the catheter. Sensors 810 are designed to contact the visceral pericardium in contact with the myocardium of a heart. Sensors 810 are designed to measure one or more dielectric and/or thermal properties of a portion of the myocardium, such as the impedance and/or conduction.

Catheter 800 may include an isolation element 812 disposed at a distal end portion thereof. Isolation element 812 is designed to physically isolate a region of the parietal pericardium from contact with a region of the visceral pericardium between sensors 810 in contact with the visceral pericardium. Optionally, isolation element 812 is designed to physically isolate a region of the parietal pericardium from contact with a region of the visceral pericardium in near proximity around the plurality of sensors in contact with the visceral pericardium, for example, a circle surrounding sensors 810.

Optionally, the isolation element is arranged to apply a contact force between sensors 810 and the visceral pericardium, for example, by a spring link action, or a pre-set bias. The force urges sensors 810 towards the parietal pericardium, which may stabilize and/or provide sufficient contact to allow for precise measurements.

Optionally, isolation element 812 is a strut (or wire) arranged in a U shape in the expanded state and straight in the contracted state. Sensors 810 may be disposed on the distal arms of the U, or in proximity to the U. The arc of the U is designed to urge the parietal pericardium away from the visceral pericardium to form the isolated region (e.g., as illustrated).

Reference is now made to FIG. 8B, which is another design of a catheter 820 (corresponding to catheter 800) for measurement of one or more dielectric and/or thermal properties of the myocardium from within the pericardial space, in accordance with some embodiments of the present invention.

Catheter 820 may include multiple arcs 822 at a distal end thereof, arranged to form a dome-like 826 shape. Electrodes 810 may be positioned within dome 826, at the flat part thereof (which is designed to contact the visceral pericardium), by extension legs 824. The curved portion of dome 826 physically isolates the parietal pericardium from the visceral pericardium within the flat part of dome 826.

Reference is now made to FIG. 8C, which is another design of a catheter 830 (corresponding to catheter 800) for measurement of one or more dielectric and/or thermal properties of the myocardium from within the pericardial space, in accordance with some embodiments of the present invention. Catheter 830 may include an expandable balloon 832. Electrodes 810 may be positioned on the outer surface of balloon 832. Expansion of balloon 832 may physically isolate the parietal pericardium from the visceral pericardium.

Some alternatives and/or optional features are now described with references to the systems and/or methods described herein. The alternatives and/or features may be executed by code stored in the program store, implementable by the processor of the computing unit. It is noted that the terms probe and catheter are sometimes interchangeable.

The method of FIG. 1 and/or system of FIG. 2 may improve the accuracy of impedance localization of an indwelling probe (e.g., navigation system 236 for the catheter) that has at least one conducting port (e.g., sensor and/or electrode) at a locatable location. The localization system may transmit and receive alternating current between ports (on the catheter and/or on another intra-body catheter, and/or at an extra-body location, e.g., body electrode patches), in one frequency or multiple different frequencies, and/or at different times, in co-planar direction (or approximately).

The localization may be performed on a probe (e.g., tool, catheter) with multiple conducting ports with predefined distances between each port. The systems and/or methods described herein may locate each port separately (optionally simultaneously or iteratively within a short period of time that appears simultaneous), making multi-pole location determination of the same probe. For example, tracked as in block 106. It is noted that the terms pole, port (e.g., conduction port), and electrode are sometimes interchangeable, for example, Pole is interchangeable with porti.

Optionally, the distances between the conducting ports is measured and/or determined, for example, downloading the specification from a remote server (e.g., via a network connection), measured using fluoroscopic measurements, and/or measured using a measuring device (e.g., ruler), and/or reading the catheter identification information from a computer readable medium (e.g., stored on the catheter itself, stored on the connector, stored on the computing unit, and/or stored remotely).

The identification of other unique properties (e.g., frequency, size) of the catheter may be derived from the inter-pole distances. For example, the inter-pole distances are used to access a record of the catheter, to determine the catheter model number. When the model number is known, other unique properties may be retrieved.

Based on the inter-pole distance, the location of each pole may be determined. The inter-pole distance may improve the accuracy of the location determination, for example, by correcting the determined location of each pole according to the known inter-pole distance.

The location of the catheter may be calibrated based on the inter-pole distance and/or based on the corrected coordinates according to the inter-pole distance, e.g., based on comparison of the calculated distance from run-time measurements to the known distance.

The code may activate the poles on the catheter and/or external poles (or another intra-body catheter, and/or extra-body poles), to transmit multiple radio waves from one or more of the poles for reception at one or more other poles. The relationship between the transmitted and received signals may be analyzed to determine characteristics of the catheter. The analysis may determine a baseline signature (e.g., relative or absolute), which serves for comparison to trace and/or monitor the multi-pole interaction with surrounding tissues and/or radio signals during the procedure, as described herein.

It is expected that during the life of a patent maturing from this application many relevant navigation systems and intrabody catheters will be developed and the scope of the terms navigation system and catheter are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computerized method of tracking a position of a catheter in a physical body portion of a patient, comprising:
    physically tracking coordinates of the position of a distal portion of a physical catheter within the physical body portion of the patient according to physically applied plurality of electrical fields within the body portion and measurements of the plurality of electrical fields performed by a plurality of physical electrodes at a distal portion of the physical catheter;
    registering the physically tracked coordinates with simulated coordinates generated according to a simulation of a simulated catheter within a simulation of the body of the patient, to identify differences between the physically tracked coordinates and the simulated coordinates;
    correcting the physically tracked coordinates according to the registered simulated coordinates; and
    providing the corrected physically tracked coordinates for presentation.

2. The method of claim 1, further comprising:
    providing a dataset of said body portion of a patient including anatomical imaging data of the patient, and at least one dielectric parameter value corresponding to one or more of different tissues of the anatomical imaging data, wherein the at least one dielectric parameter value represents an initial estimated value; and
    generating the simulation that tracks coordinates of a position of the simulated catheter within the dataset representing the body portion according to simulated application of a plurality of electrical fields within the body portion and measurements of the plurality of electrical fields performed by a plurality of electrodes at a distal portion of the catheter.

3. The method of claim 2, wherein the dataset includes at least one thermal parameter corresponding to the one or more of different tissues of the anatomical imaging data, wherein the at least one thermal parameter affects the at least one dielectric parameter value, and wherein generating comprises generating the simulation according to simulated values of the at least one thermal parameter.

4. The method of claim 1, wherein the simulation includes a simulation of a plurality of extra-body electrodes that generate the plurality of electrical fields.

5. The method of claim 4, further comprising:
executing the simulation by varying at least one parameter of at least one of the extra-body electrodes, estimating an inaccuracy in simulated coordinates in proximity to a target tissue, repeating the simulation and the estimating by varying at least one of parameters, and selecting the at least one varied parameter to reduce the inaccuracy.

6. The method of claim 5, wherein the at least one parameter of at least one of the simulated extra-body electrodes varied in said executing the simulation is selected from the group consisting of extra-body electrode location, size of transmitting extra-body electrode surface area, geometry of transmitting extra-body electrode surface area, electric field strength of an extra-body electrode, electric current amplitude of an extra-body electrode, and frequency of electric current of an extra-body electrode.

7. The method of claim 1, wherein the simulation includes a simulation of at least one parameter that modifies the measurements of the plurality of electrical fields and/or modifies a dielectric measurement of tissue in said body portion, and further comprising executing the simulation by varying the at least one parameter, estimating an inaccuracy in simulated coordinates in proximity to a target tissue, repeating the simulation and the estimating by varying at least one of the at least one parameters, and selecting the at least one varied parameter to reduce the inaccuracy.

8. The method of claim 7, wherein the at least one parameter is selected from the group consisting of location of multiple catheters in said body portion, effect of drugs on said body portion, effect of disease on said body portion, effect of pre-applied treatments on said body portion, effect of mechanical force applied to tissues of said body portion, effect of applying a thermal intervention on said body portion, effect of transmitting signal(s) into the body portion, and effect of transmitting signal(s) out of the body portion.

9. The method of claim 1, further comprising injecting a predefined signal to a plurality of extra-body electrodes used generate the plurality of electrical fields, using the injected signal to analyze the effects before, during, and/or after an ablation procedure on measurements of the plurality of electrical fields, and correcting the physically tracked location coordinates according to the analysis.

10. The method of claim 1, wherein registering further comprises calibrating the simulated coordinates according to a defined anatomical and physical location of the distal end portion of the physical catheter.

11. The method of claim 1, wherein the simulation includes determining for tissue being ablated according to the corrected physically tracked location coordinates, at least one of: a power loss density (PLD) pattern, a gasification transition, and a temperature pattern.

12. The method of claim 1, further comprising:
receiving a real-time measurement of at least one dielectric parameter of at least one intra-body tissue;
generating an updated simulation by updating an initial estimated value of the at least one dielectric parameter value with the real-time measurement; and
repeating the registering and the correcting.

13. The method of claim 12, wherein the registering and the correcting are repeated until a stop condition is met, wherein the stop condition is identified by matching of a predefined signal template indicative of achievement of a desired ablation pattern to sensed signals and/or measurements.

14. The method of claim 13, wherein the matched predefined signal template is indicative of at least one of: tissue coagulation, tissue edema, transmural ablation, continuous ablation line, safety indicator, and procedure effectiveness indicator.

15. The method of claim 13, wherein the at least one dielectric parameter is at least one of impedance and conductivity, and the at least one intra-body tissue is at least one of blood and myocardium.

16. The method of claim 13, wherein the generating, the registering, and the correcting are performed for a sub-volume that includes a target tissue in proximity to the distal end of the physical catheter.

17. The method of claim 16, wherein the generating, the registering, and the correcting are iteratively performed with decreasing volumes of the sub-volume as the distance between the distal end of the physical catheter and the target tissue decreases.

18. The method of claim 17, wherein the iterations are performed to achieve an accuracy of about +/−1 millimeter of the corrected physically tracked coordinates.

19. The method of claim 1, further comprising:
measuring a thickness of a tissue including a target tissue according to a dataset including anatomical image data of the patient;
iteratively receiving, from at least one electrode of the physical catheter, at least one measurement of at least one dielectric parameter of tissue in proximity to the target tissue within said body portion, the at least one measurement performed before an ablation of the target tissue, during the ablation, and after the ablation; and
iteratively correlating the measured thickness with the received at least one electrical parameter to estimate at least one of a lesion volume and a lesion depth.

20. The method of claim 19, wherein the simulation includes a simulated ablation of the target tissue according to a simulated optimal contact force between the distal end portion of the simulated catheter and tissue in proximity to the target tissue, and further comprising correlating the at least one dielectric parameter to estimate a quality of the contact force relative to the simulated optimal contact force.

21. The method of claim 20, wherein the estimated quality of the contact force is selected from the group consisting of suboptimal contact force, optimal contact force, and excessive contact force.

22. The method of claim 21, wherein the simulation is according to at least one ablation parameter.

23. The method of claim 20, wherein the at least one measurement is performed in at least two frequencies.

24. The method of claim 1, further comprising:
iteratively receiving, from at least one electrode of the physical catheter during the physically tracking, a plurality of measurements of a dielectric parameter of tissue in proximity to a target tissue, each of the plurality of measurements performed at a respective location in proximity to the target tissue and associated with said respective location;
analyzing the measurements and their association with each of the plurality of locations to identify an electrical tissue signature indicative of at least one fibrotic tissue region; and
mapping the at least one fibrotic tissue region to a dataset including anatomical image data of the patient, for display.

25. The method of claim 1, further comprising:
analyzing a trajectory of the physically tracked coordinates of the position of a distal portion of a physical catheter over a time range including at least one cardiac cycle; and
estimating a quality of contact between the distal portion of the physical catheter and a pulsating tissue portion according to the analyzed trajectory.

26. The method of claim 25, wherein analyzing comprises:
at least one of measuring and simulating motion of the pulsating tissue over the time range;
and correlating the physically tracked coordinates of the position of the distal portion with the motion of the pulsating tissue.

27. The method of claim 26, wherein measuring of the pulsating tissue is performed according to gating of a real-time ECG measurement.

28. The method of claim 1, wherein the body portion includes a heart and the simulation includes tracking coordinates of navigation of the simulated catheter within the heart for an intra-cardiac ablation procedure.

29. The method of claim 2, wherein the at least one dielectric parameter value includes an impedance value of the respective tissue.

30. The method of claim 1, wherein the physically tracking is based on impedance based mapping techniques.

31. A computerized method for tracking a position of an intra-body catheter, comprising:
receiving location coordinates of said intra-body catheter within a body of a patient, the location coordinates measured based on applied electric fields; and
correcting the location coordinates according to a simulation of the intra-body catheter within the body based on a dielectric map including acquired anatomical imaging data of the patient and at least one dielectric parameter value corresponding to one or more different tissues identified within the anatomical imaging data.

32. A computerized method of tracking a position of a catheter in a body portion of a patient, comprising:
applying a plurality of electrical fields to the body portion of the patient; tracking physical coordinates of a position of a distal portion of the catheter within the body portion of the patient based upon measurements of the plurality of electrical fields;
registering the physically tracked coordinates with simulated coordinates obtained from a simulation of a simulated catheter within a simulated body of the patient, to identify differences between the physically tracked coordinates and the simulated coordinates;
correcting the physically tracked coordinates based upon the differences between the physically tracked coordinates and the simulated coordinates; and
providing the corrected tracked coordinates for presentation.

* * * * *